(12) United States Patent
Diwu et al.

(10) Patent No.: US 8,093,411 B2
(45) Date of Patent: *Jan. 10, 2012

(54) CYANINE DYES AND THEIR APPLICATIONS AS LUMINESCENCE QUENCHING COMPOUNDS

(75) Inventors: Zhenjun Diwu, Sunnyvale, CA (US); Jianheng Zhang, Santa Clara, CA (US); Yi Tang, Sunnyvale, CA (US)

(73) Assignee: AnaSpec Incorporated, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/807,180

(22) Filed: Aug. 30, 2010

(65) Prior Publication Data

US 2010/0331543 A1 Dec. 30, 2010

Related U.S. Application Data

(63) Continuation of application No. 11/222,049, filed on Sep. 7, 2005, now Pat. No. 7,910,753.

(60) Provisional application No. 60/608,817, filed on Sep. 10, 2004.

(51) Int. Cl.
*C07D 209/46* (2006.01)
*C07D 209/02* (2006.01)

(52) U.S. Cl. ............................. 549/472; 548/465

(58) Field of Classification Search .............. 546/79, 546/112; 514/290; 549/472; 548/485
See application file for complete search history.

(56) References Cited

U.S. PATENT DOCUMENTS

| | | | |
|---|---|---|---|
| 3,521,187 A | 7/1970 | Snavely et al. | |
| 3,821,233 A | 4/1972 | Lincoln et al. | |
| 3,753,721 A | 8/1973 | Millikan et al. | |
| 3,854,956 A | 12/1974 | Lincoln et al. | |
| 3,864,644 A | 2/1975 | Lincoln et al. | |
| 3,904,637 A | 9/1975 | Lincoln et al. | |
| 3,915,715 A | 10/1975 | Millikan et al. | |
| 5,538,848 A | 7/1996 | Livak et al. | |
| 5,627,027 A | 5/1997 | Waggoner et al. | |
| 5,658,735 A | 8/1997 | Lee | |
| 5,760,201 A | 6/1998 | Glazer et al. | |
| 6,048,982 A | 4/2000 | Waggoner et al. | |
| 6,133,445 A | 10/2000 | Waggoner et al. | |
| 6,207,464 B1 | 3/2001 | Karandikar et al. | |
| 6,329,144 B1 | 12/2001 | Kubista et al. | |
| 6,573,374 B1 | 6/2003 | Muehlegger et al. | |
| 6,750,024 B2 | 6/2004 | Lee et al. | |
| 6,790,660 B1 | 9/2004 | Yu et al. | |
| 7,465,810 B2 * | 12/2008 | Diwu et al. | 548/418 |
| 7,473,415 B2 * | 1/2009 | Kawakami et al. | 424/9.6 |

OTHER PUBLICATIONS

De Angelis, D., "Why FRET over genomics" A. Physiol Genomics (1999) 1:93-9.

Didenko, V. V., "DNA probes using fluorescence resonance energy transfer (FRET): designs and applications" Biotechniques (2001) 31:1106-16, 1118, 1120-1.

Tian, H., "Fluorescence lifetimes of supersensitizing systems and dyes adsorbed into TiO2" (1992) J. Photochem. Photobiol. A, 65:399-407.

Emptage, N., "Fluorescent imaging in living systems" J. Curr Opin Pharmacol (2001) 1:521-5.

Holskin, B. P., "A continuous fluorescence-based assay of human cytomegalovirus protease using a peptide substrate" (1995) Anal. Biochem, 226:148-155.

Klostermeier, D., Miller D.P., "Time-resolved fluorescence resonance energy transfer: a versatile tool for the analysis of nucleic acids" Biopolymers (2001) 61:159-79.

Gulnik, S. V., et al., "Design of sensitive fluorogenic substrates for human cathepsin D" (1997) FEBS Lett 413:379-384.

Beekman, B., et al., "Highly increased levels of active stromelysin in rheumatoid synovial fluid determined by a selective . . . " (1997) FEBS Lett, 418:305-309.

Beebe, K.D., "A continuous fluorimetric assay for tail-specific protease" (1998) Anal Biochem, 263:51-56.

Beekman, B., "Convenient fluorometric assay for matrix metalloproteinase activity and its application in biological media" (1996) FEBS Lett 390, 221-225.

\* cited by examiner

*Primary Examiner* — Nizal Chandrakumar
(74) *Attorney, Agent, or Firm* — Jeffrey A. McKinney; McKinney Law Group APC

(57) ABSTRACT

The quenching compounds of the invention are weakly luminescent cyanines that are substituted by one or more heteroaromatic quenching moieties. The quenching compounds of the invention exhibit little or no observable luminescence and efficiently quench a broad spectrum of luminescent compounds. The chemically reactive quenching compounds possess utility for labeling a wide variety of substances, including biomolecules. These labeled substances are highly useful for a variety of energy-transfer assays and applications.

10 Claims, 11 Drawing Sheets

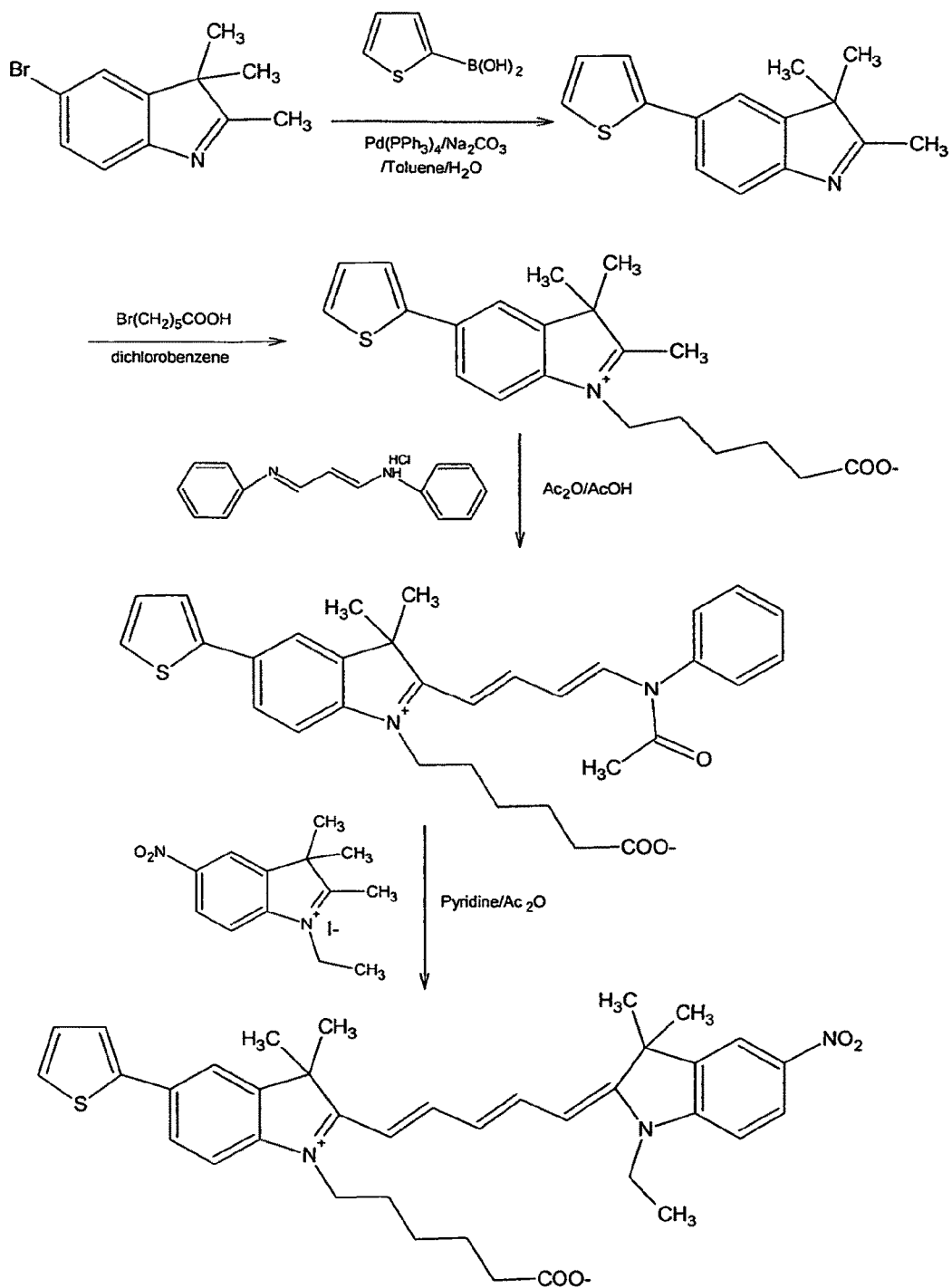
FIG. 1. Synthesis of a cyanine that has a RM at 1-position

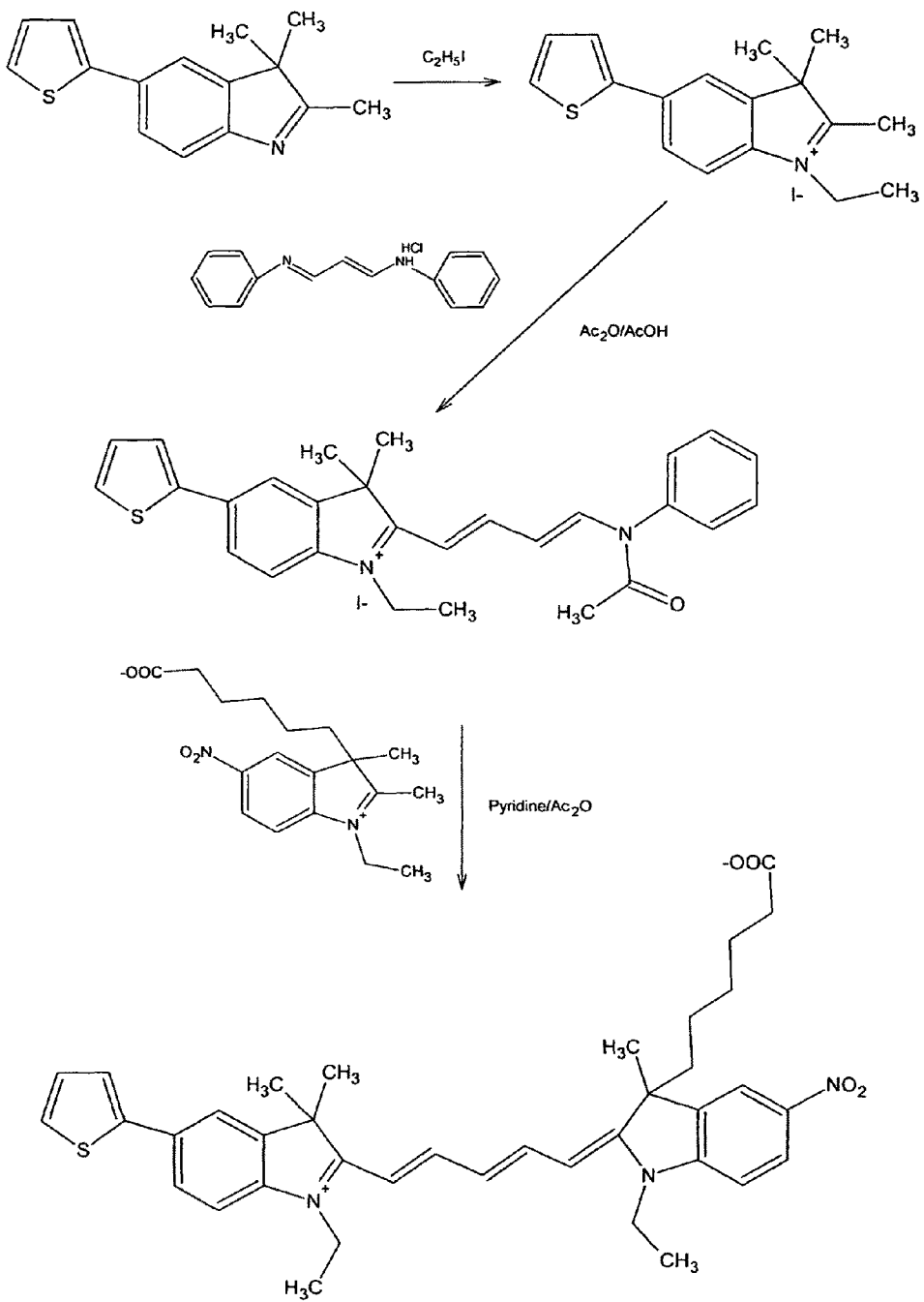
FIG. 2. Synthesis of a cyanine that has a RM at 3-position

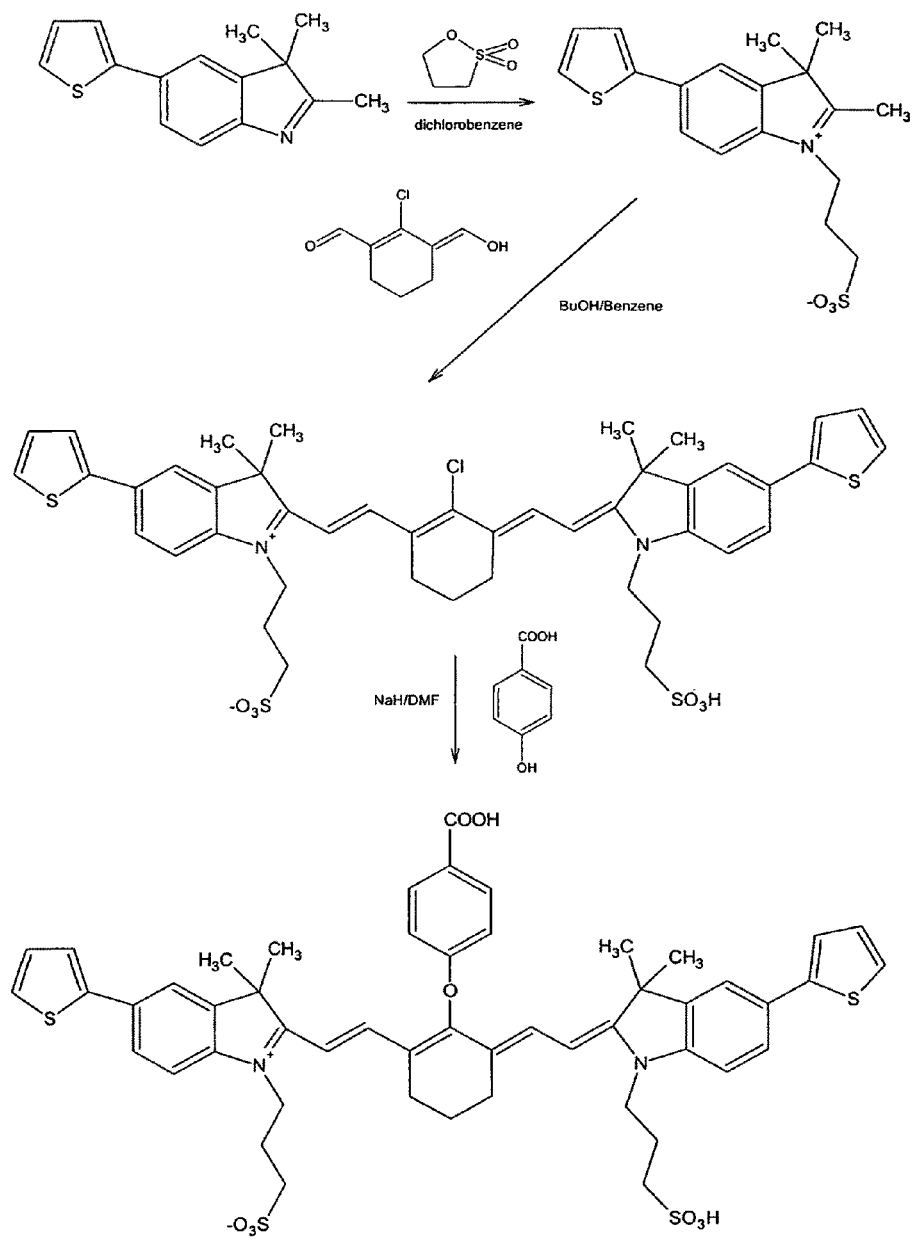
FIG. 3. Synthesis of a cyanine that has a RM at the BRIDGE atoms

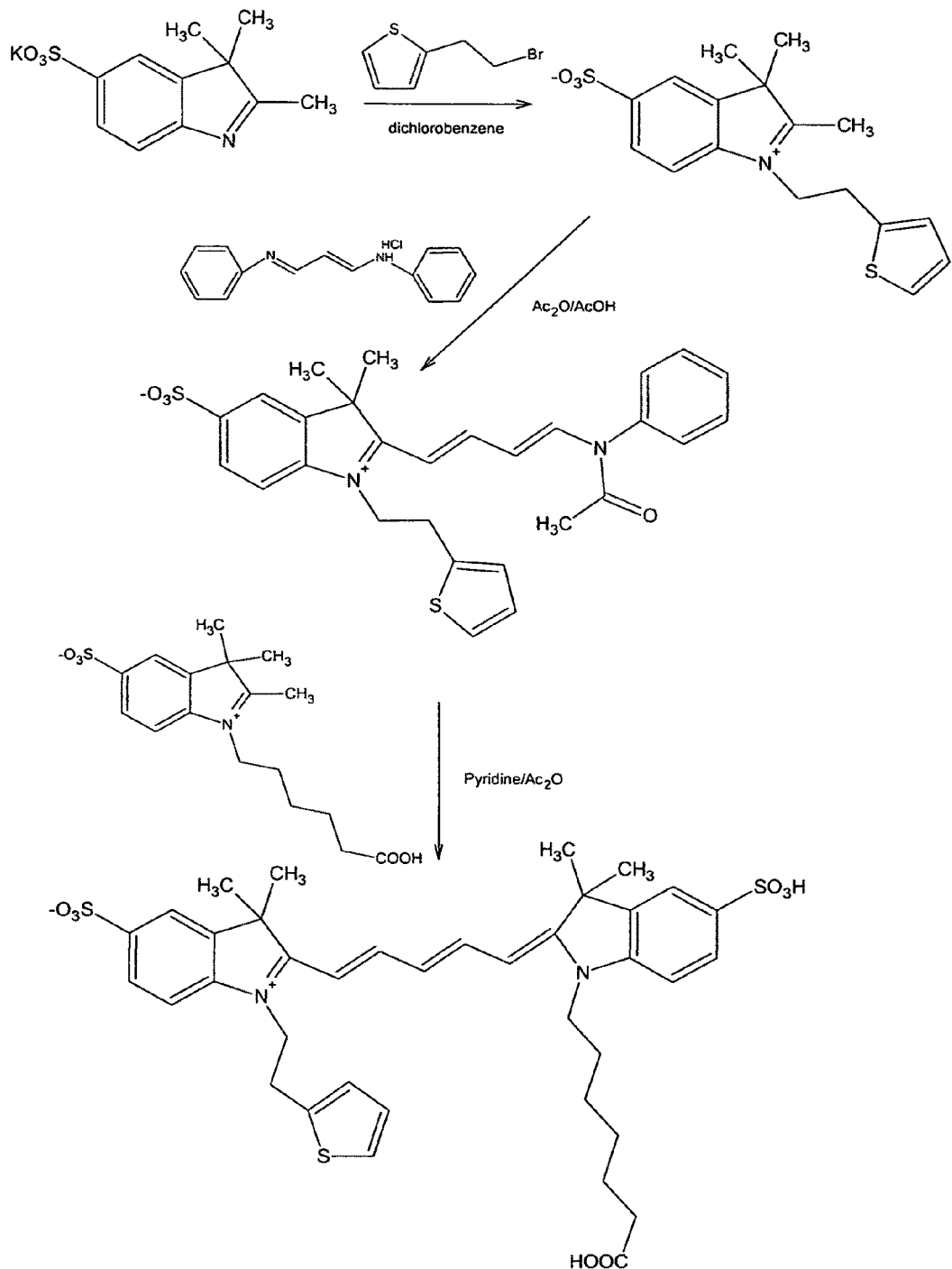
FIG. 4. Synthesis of a cyanine that has a LQM at 1-position

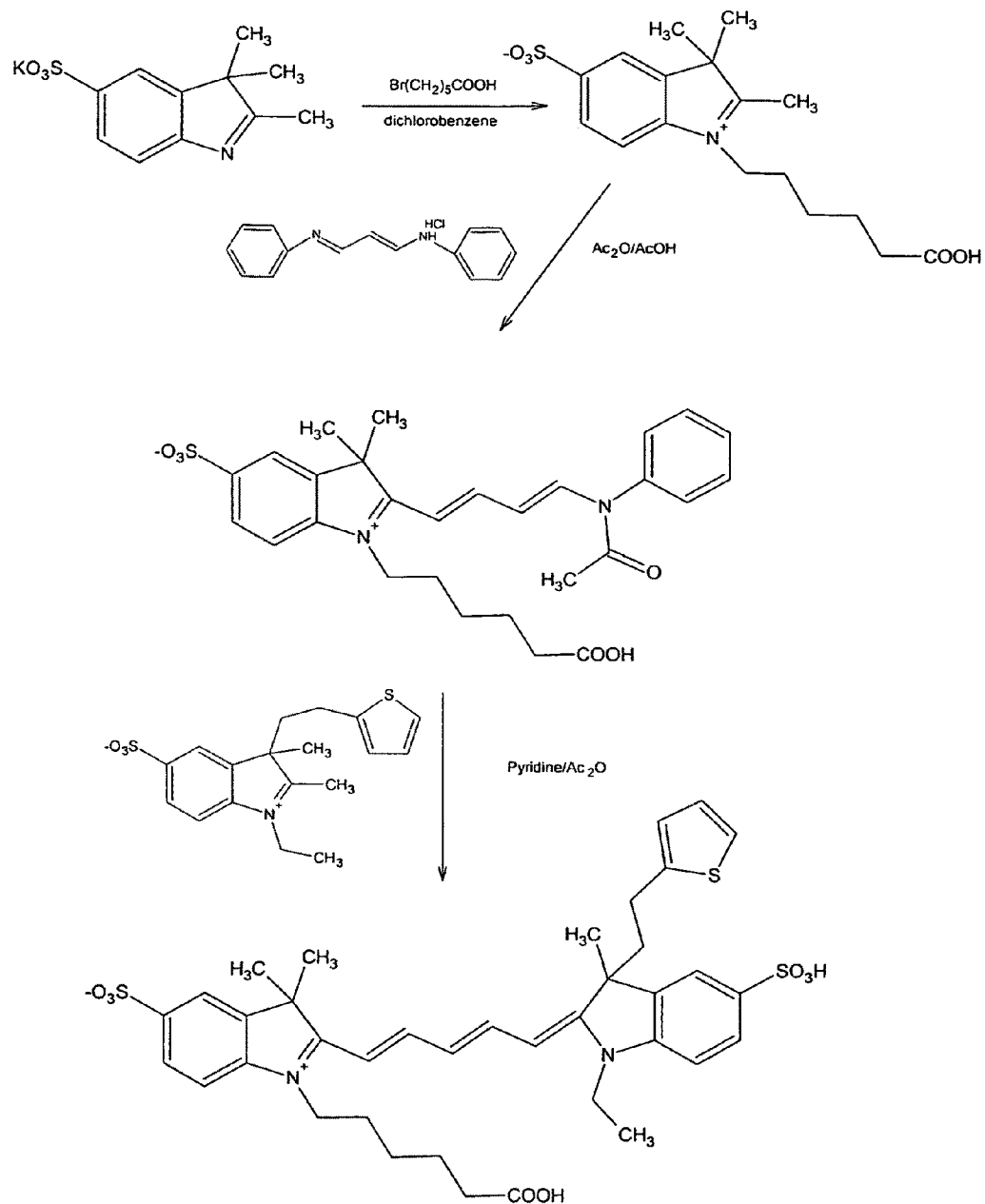
FIG. 5. Synthesis of a cyanine that has a LQM at 3-position

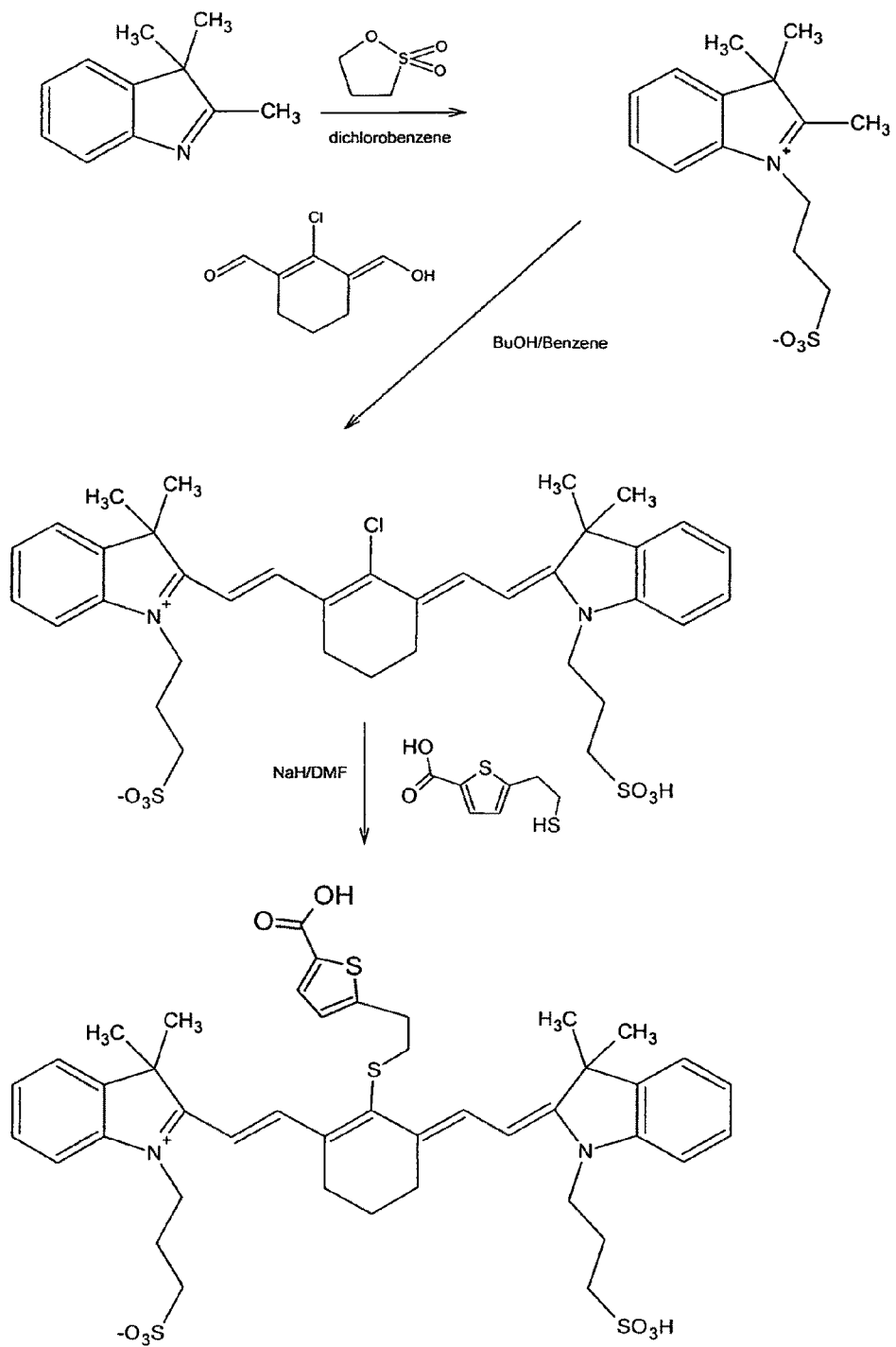
FIG. 6. Synthesis of a cyanine that has a LQM at the BRIDGE atoms

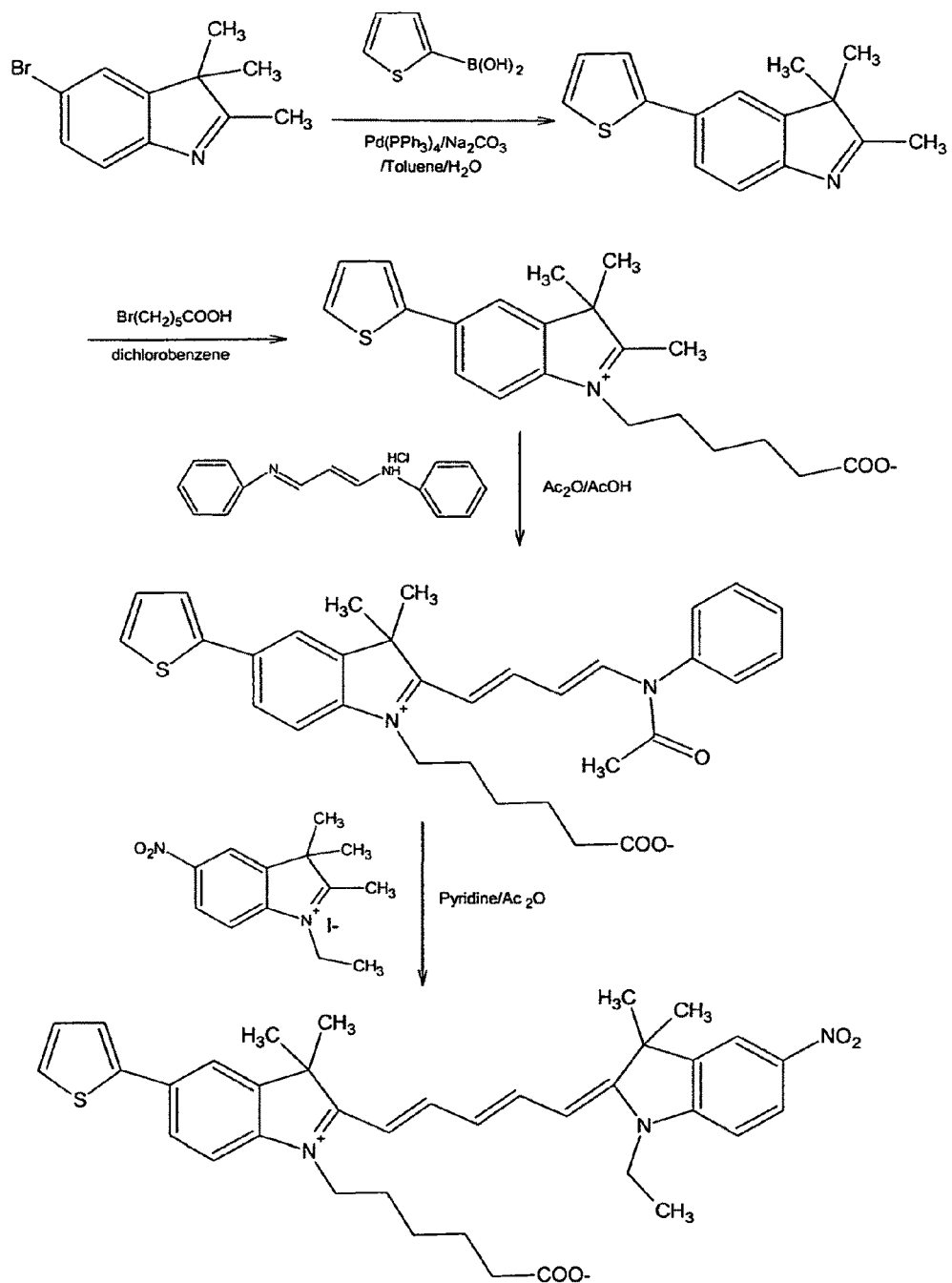
FIG. 7. Synthesis of a cyanine that has a LQM at Ring A or Ring B

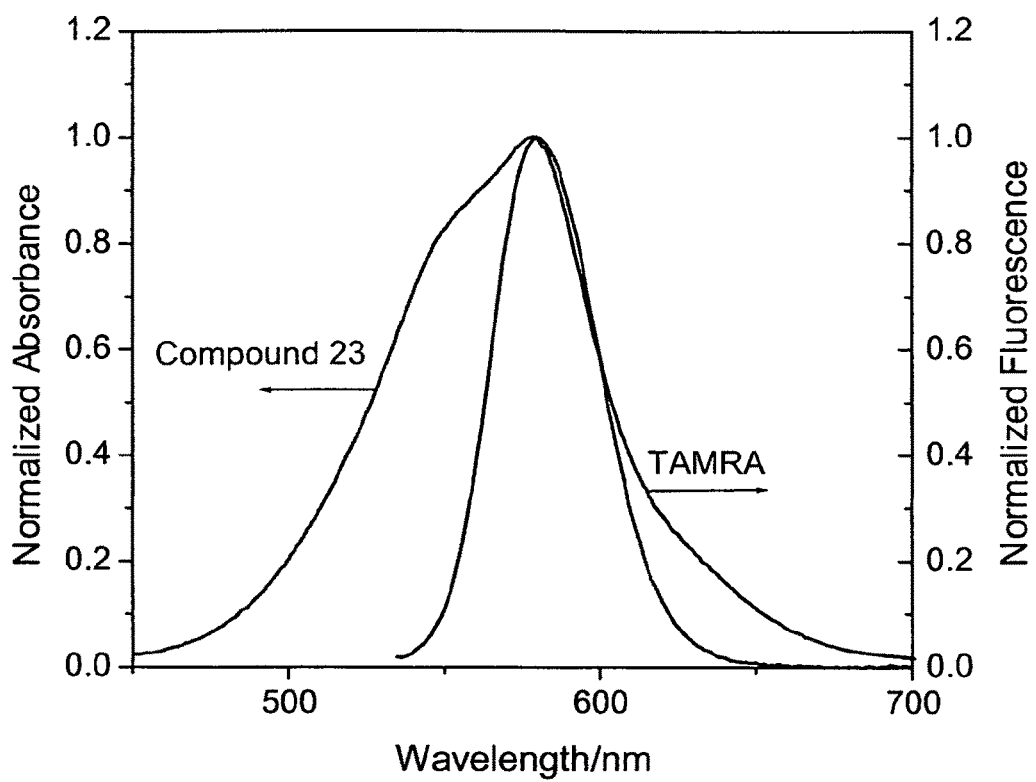
FIG. 8. Spectral overlap of compound 23 with 5-TAMRA

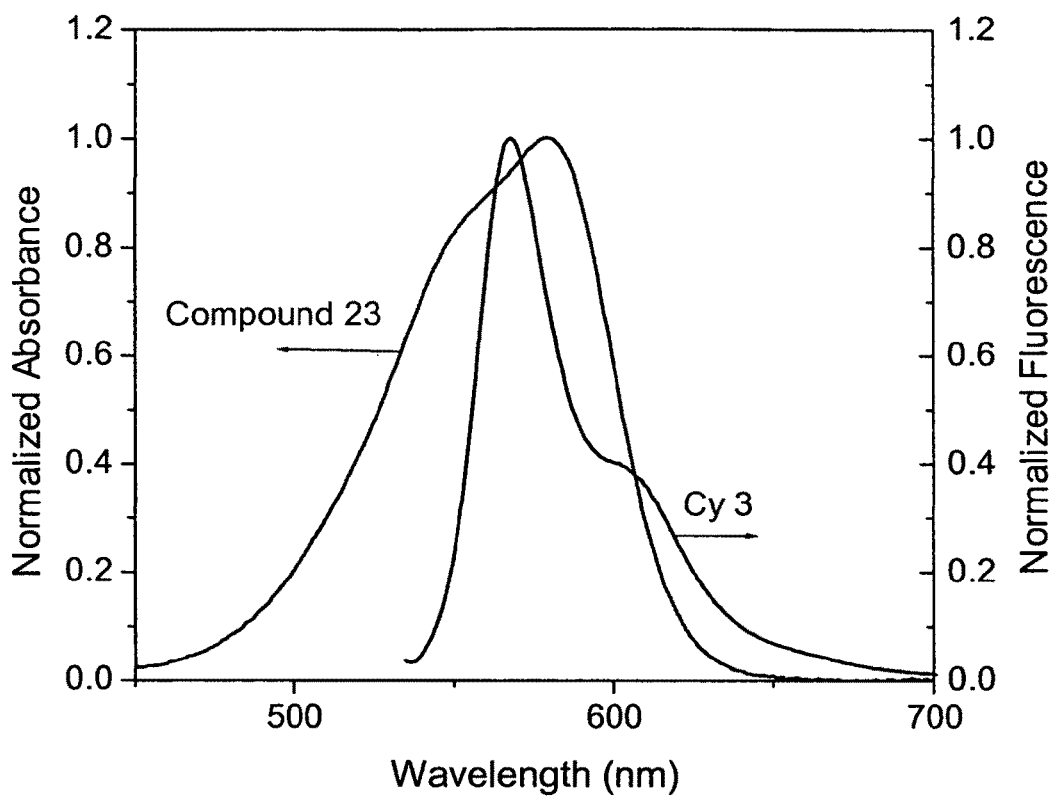
FIG. 9. Spectral overlap of compound 23 with Cy3

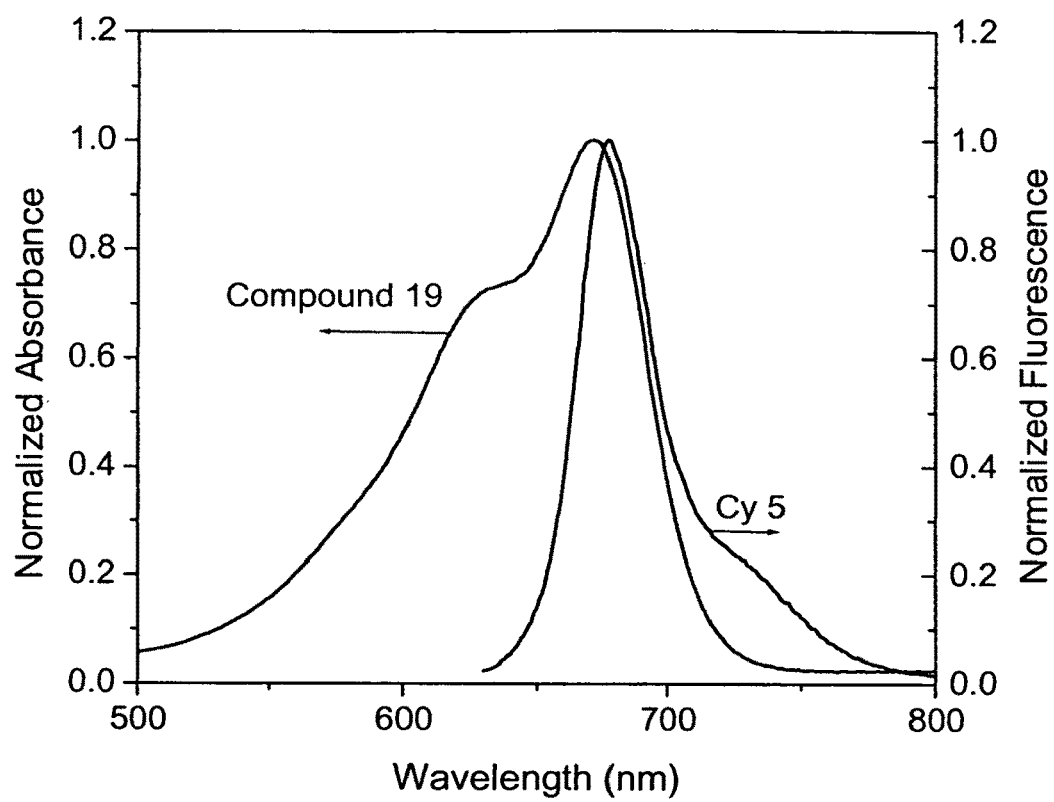
FIG. 10. Spectral overlap of compound 19 with Cy5.

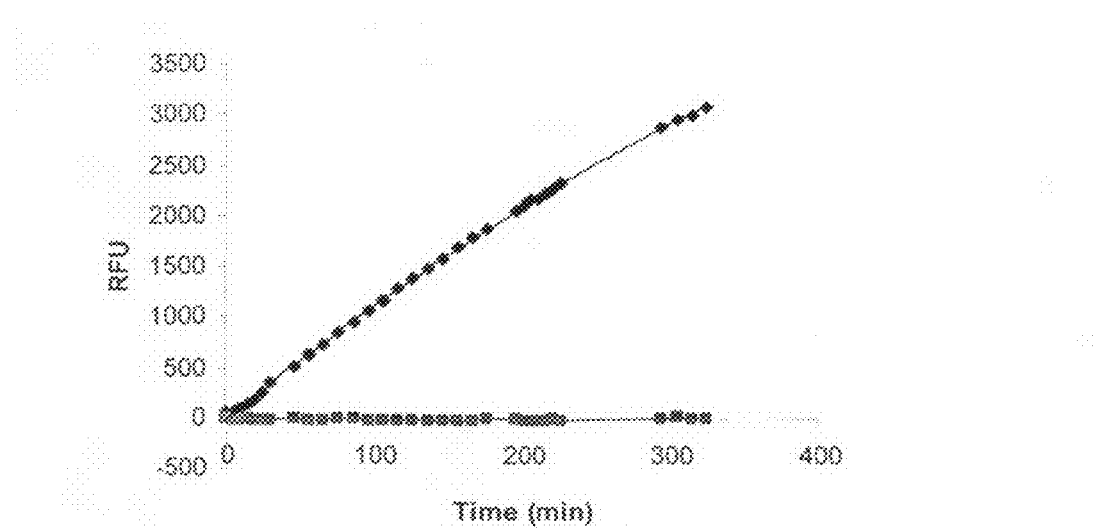
FIG. 11. MMP-2 cleavage of Compound 19-Lys-Pro-Leu-Ala-Nva-Asp(Cy5)-Ala-Arg-NH2.

CYANINE DYES AND THEIR APPLICATIONS AS LUMINESCENCE QUENCHING COMPOUNDS

This application is a continuation of, and accordingly claims priority from, U.S. patent application Ser. No. 11/222,049, filed Sep. 7, 2005 now U.S. Pat. No. 7,910,753, which claims priority from U.S. Provisional Patent Appl. No. 60/608,817, filed Sep. 10, 2004, the subject matter of each being incorporated herein by reference in their entirety.

FIELD OF THE INVENTION

The invention relates to cyanine compounds that are efficient quenchers of luminescence. Chemically reactive versions of the cyanine compounds are described, as are conjugates prepared using the reactive compounds. Applications using the cyanine quenching compounds are also described.

BACKGROUND

Fluorescence Resonance Energy Transfer (FRET) is a process whereby a first fluorescent dye (the "donor" dye) is excited, typically by illumination, and transfers its absorbed energy to a second dye (the "acceptor" dye) that has a longer wavelength and therefore lower energy emission. Where the second dye is fluorescent, energy transfer results in fluorescence emission at the wavelength of the second dye. However, where the second dye is nonfluorescent, the absorbed energy does not result in fluorescence emission, and the fluorescence of the initial donor dye is said to be "quenched". Energy transfer can also be utilized to quench the emission of luminescent donors, including phosphorescent and chemiluminescent donors. When a luminescent emission is restored by preventing energy transfer, the luminescence is said to be "dequenched" or "unquenched".

The use of a variety of dyes to quench fluorescence is known in the art. The application of this phenomenon to analyze biological systems is also well-detailed. FRET has been utilized to study DNA hybridization and amplification, the dynamics of protein folding, proteolytic degradation, and interactions between other biomolecules (Methods in Enzymology, Vol. 278). By far the most common donor-acceptor dye pair utilized for these applications is dabcyl (the quenching dye) and EDANS (the fluorophore) (as discussed in The FRET Probes, AnaSpec, 2004). Selected examples of biological applications of FRET can be found in the following references, among others:

(1) Holskin, B. P.; Bukhtiyarova, M.; Dunn, B. M.; Baur, P.; Dechastonay, J.; Pennington, M. W. Anal Biochem 1995, 227,148-155.

(2) Beekman, B.; Drijthout, J. W.; Bloemhoff, W.; Ronday, H. K.; Tak, P. P.; to Koppele, J. M. FEBS Lett 1996, 390, 221-225.

(3) Pennington, M. W.; Thornberry, N. A. Peptide Research 1994, 7, 72-76.

(4) Wang, Q. M.; Johnson, R. B.; Cohen, J. D.; Voy, G. T.; Richardson, J. M.; Jungheim, L. N. Antivir Chem Chemother 1997, 8, 303-310.

(5) Gulnik, S. V.; Suvorov, L. I.; Majer, P.; Collins, J.; Kane, B. P.; Johnson, D. G.; Erickson, J. W. FEBS Lett 1997, 413, 379-384.

(6) Beekman, B.; van El, B.; Drijthout, J. W.; Ronday, H. K.; TeKoppele, J. M. FEBS Lett 1997, 418, 305-309.

(7) Beebe, K. D.; Pei, D. Anal Biochem 1998, 263, 51-56.

Despite the widespread use of the dabcyl-EDANS energy transfer pair, this technology possesses a number of shortcomings. For most applications, the use of low wavelength excitation is not optimal due to the autofluorescence exhibited by most cellular systems. Ultraviolet light can also cause DNA cross-linking in some systems. In addition, if low wavelength excitation is used in a drug screening assay, many drugs, potential drugs, and biologically active proteins have very strong absorptions in the low wavelength region. Both dabcyl and EDANS have low extinction coefficients, resulting in assays that are comparatively insensitive.

In order to avoid the difficulties associated with the use of ultraviolet excitation, the absorption of the energy acceptor should be closely aligned with the visible light fluorophore used. The compounds of the instant invention have been discovered to quench the fluorescence of a large variety of dyes, including dyes that are excited in the ultraviolet, but also including fluoresceins, rhodamines, and even longer wavelength fluorophores such as Cy5 and allophycocyanin. In addition, the compounds of the invention have significantly larger extinction coefficients than the quenching compounds that are typically currently used in energy transfer assays.

The compounds of the instant invention represent a new and highly useful class non-fluorescent energy acceptors, including chemically reactive versions, and the conjugates prepared therefrom.

References Cited

| U.S. Patent Documents | | |
|---|---|---|
| 3,753,721 | August, 1973 | Millikan et al. |
| 3,821,233 | June, 1974 | Lincoln et al. |
| 3,854,956 | December, 1974 | Lincoln et al. |
| 3,864,644 | February, 1975 | Lincoln et al. |
| 3,904,637 | September, 1975 | Lincoln et al. |
| 3,915,715 | October 1975 | Millikan et al. |
| 5,627,027 | May, 1997 | Waggoner et al. |
| 6,048,982 | April, 2000 | Waggoner et al. |
| 6,133,445 | May, 2001 | Waggoner et al. |
| 6,750,024 | June, 2004 | Lee et al. |
| Foreign Patent Documents | | |
| 22 13 715 | October 1972 | DE. |
| 0 747 448 | December, 1996 | EP. |
| 97 17471 | May, 1997 | WO. |
| 95/04747 | February, 1995 | WO. |
| 96/04405 | February 1996 | WO. |
| 96/15270 | May, 1996 | WO. |
| 97/45539 | December, 1997 | WO. |
| 02/26891 | September, 2001 | WO. |

Other References

De Angelis D. A. *Physiol Genomics*, 1, 93-9 (1999).

Didenko V. V. *Biotechniques*, 31, 1106-16, 1118, 1120-1 (2001).

Dietrich A., et al., *J. Biotechnol*, 82, 211-31 (2002).

Emptage N. J. *Curr Opin Pharmacol*, 1, 521-5 (2001).

Ha T. *Methods*, 25, 78-86 (2001).

Klostermeier D., Millar D. P. *Biopolymers*, 61, 149-79 (2001).

Lakowicz J. R. *Principles of Fluorescence Spectroscopy*. Kluwer Academic/Plenum Publishers, New York (1999).

Majumdar R. B. et al., *Bioconjugate Chem*, 2, 105-111 (1993).

He Tian et al., *J. Photographic Sci.* 40, 100-104 (1992).

O'Brien et al., *Carbocyanine Dyes and the Energy-Transfer Mechanism of Spectral Sensitization*, Vol. 18, No. 1, pp. 76-85 (1974).

Tian H., *J. Photochem. Photobiol.* A 65, 399-407 (1992).

Gulnik, S. V.; Suvorov, L. I.; Majer, P.; Collins, J.; Kane, B. P.; Johnson, D. G.; Erickson, J. W. *FEBS Lett* 413, 379-384 (1997).

Beekman, B.; van El, B.; Drijfhout, J. W.; Ronday, H. K.; TeKoppele, J. M., *FEBS Lett* 418, 305-309 (1997).

Beebe, K. D.; Pei, D. *Anal Biochem* 263, 51-56 (1998).

Tyagi, et al., *Nature Biotechnology* 16, 49 (1998).

Brinkley, *Bioconjugate Chem.*, 3, 2 (1992).

Haugland, *Meth. Mol. Biol.* 45, 205 (1995).

Holskin, B. P.; Bukhtiyarova, M.; Dunn, B. M.; Baur, P.; Dechastonay, J.; Pennington, M. W. *Anal. Biochem* 226, 148-155 (1995).

Beekman, B.; Drijfhout, J. W.; Bloemhoff, W.; Ronday, H. K.; Tak, P. P.; to Koppele, J. M. *FEBS Lett* 390, 221-225 (1996).

Pennington, M. W., Thornberry, N. A. *Peptide Research* 7, 72-76 (1994).

BRIEF DESCRIPTION OF THE DRAWINGS

FIG. 1. Synthesis of a cyanine that has a RM at 1-position.

FIG. 2. Synthesis of a cyanine that has a RM at 3-position.

FIG. 3. Synthesis of a cyanine that has a RM at the BRIDGE atoms.

FIG. 4. Synthesis of a cyanine that has a LQM at 1-position.

FIG. 5. Synthesis of a cyanine that has a LQM at 3-position.

FIG. 6. Synthesis of a cyanine that has a LQM at the BRIDGE atoms.

FIG. 7. Synthesis of a cyanine that has a LQM at Ring A or Ring B.

FIG. 8. Spectral overlap of compound 23 with 5-TAMRA in MeOH.

FIG. 9. Spectral overlap of compound 23 with Cy3 in MeOH.

FIG. 10. Spectral overlap of compound 19 with Cy5 in MeOH.

FIG. 11. MMP-2 cleavage of Compound 19-Lys-Pro-Leu-Ala-Nva-Asp(Cy5)-Ala-Arg-$NH_2$). 50 μM of the FRET peptide is incubated with 4 nM MMP-2 (blue square) or without MMP-2 (pink square) at room temperature. The fluorescence signal is recorded on a fluorescence microplate reader at Ex/Em=650±40 nm/670±40 nm. The recording is started as soon as the enzymatic reaction is initiated.

SUMMARY OF THE INVENTION AND DESCRIPTION OF THE PREFERRED EMBODIMENTS

The present invention comprises cyanine dyes that incorporate both a heterocyclic luminescence-quenching moiety (LQM) and a chemically reactive moiety (RM). The dyes of the invention are only weakly fluorescent or virtually non-fluorescent, and typically have Formula I:

Formula I

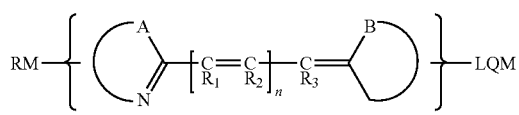

wherein A represents the atoms necessary to form a nitrogen-containing five-membered heterocyclic ring that has zero to three fused aromatic rings having 6 atoms in each ring selected from the group consisting of C, CH, $CH_2$, C(alkyl)$_2$, O, S, NH and N-alkyl provided that said five-membered ring contains =N(alkyl) coupled to the bridged and conjugated double bonds, wherein aromatic carbon atoms are optionally substituted one or more times by substituents selected from the group consisting of hydrogen, alkyl having from 1-20 carbons, alkoxy having from 1-20 carbons, trifluoromethyl, halogen, methylthio, sulfonyl, carbonyl, hydroxy, amino, thiol, RM and LQM.

B is selected from a conjugated cyclic moiety that has a condensable carbon atom of 2-alkylindolium, 2-alkylbenzothiazolium, 2-alkylbenzoimidazolium, 2-alkylbenzoxazolium, barbituric acid, thiobarbituric acid, α-cyanocarbonyl compounds and α,β-dicarbonyl (e.g. malonyl compounds), wherein carbon or nitrogen atoms are optionally substituted one or more times by substituents selected from the group consisting of hydrogen, alkyl having from 1-20 carbons, alkoxy having from 1-20 carbons, trifluoromethyl, halogen, methylthio, sulfonyl, carbonyl, hydroxy, amino, thiol, RM and LQM.

n is 0 to 3.

$R_1$, $R_2$, and $R_3$ are independently selected from the group consisting of hydrogen, alkyl having 1-6 carbons, cycloalkyl having 3-10 carbons, aryl, heteroaryl, RM and LQM RM is a chemically reactive group;

LMQ is a heterocyclic moiety that quenches luminescence of said chromophore (in large bracket in Fromula I).

The dyes of the invention comprise a cyanine dye that contains: 1) a LQM group; 2) a bridging methane; and 3) a RM group. There are two ring systems in the compounds of the invention. In one embodiment of the invention, the first or second ring system is substituted by a side chain that contains a LQM group. In another embodiment, the first or second ring system is substituted by a side chain that contains a RM group. In another embodiment, the bridged methine is substituted by a side chain that contains a RM group. In another embodiment, the bridged methine is substituted by a side chain that contains a LQM group.

Preferred compounds have at least one substituted indolium ring system wherein the substituent contains a RM and a LQM. Other preferred compounds incorporate at least a charged group (e.g., sulfonate and ammonium moieties) to increase water solubility. By "sulfo" is meant sulfonic acid, or salt of sulfonic acid (sulfonate). Similarly, by "carboxy" is meant carboxylic acid or salt of carboxylic acid. "Phosphate", as used herein, is an ester of phosphoric acid, and includes salts of phosphate. "Phosphonate", as used herein, means phosphonic acid and includes salts of phosphonate. As used herein, unless otherwise specified, the alkyl portions of substituents such as alkyl, alkoxy, arylalkyl, alylamino, dialkylamino, trialkylammonium, or perfluoroalkyl are optionally saturated, unsaturated, linear or branched, and all alkyl, alkoxy, alkylamino, and dialkylamino substituents are themselves optionally further substituted by carboxy, sulfo, amino, or hydroxy.

A preferred embodiment is a compound of Formula II:

Formula II

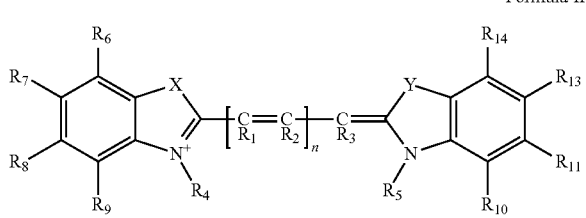

wherein $R_1$ to $R_{17}$ are hydrogen, alkyl having from 1-20 carbons, alkoxy having from 1-20 carbons, trifluoromethyl, halogen, methylthio, sulfonyl, carbonyl, hydroxy, amino, thiol, RM and LQM; X and Y are $CR_{15}R_{16}$, $NR_{17}$, O and S; n is 0 to 3.

Another preferred embodiment is a compound of Formula III:

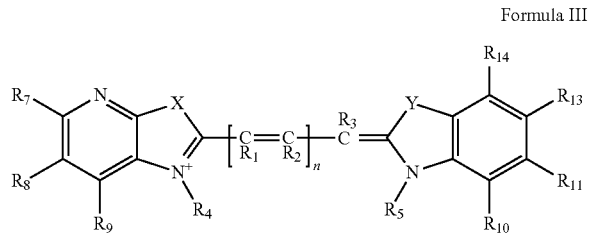

Formula III wherein $R_1$ to $R_{17}$ are hydrogen, alkyl having from 1-20 carbons, alkoxy having from 1-20 carbons, trifluoromethyl, halogen, methylthio, sulfonyl, carbonyl, hydroxy, amino, thiol, RM and LQM; X and Y are $CR_{15}R_{16}$, $NR_{17}$, O and S; n is 0 to 3.

Another preferred embodiment is a compound of Formula IV:

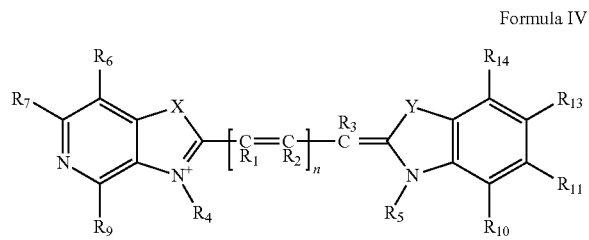

Formula IV wherein $R_1$ to $R_{17}$ are hydrogen, alkyl having from 1-20 carbons, alkoxy having from 1-20 carbons, trifluoromethyl, halogen, methylthio, sulfonyl, carbonyl, hydroxy, amino, thiol, RM and LQM; X and Y are $CR_{15}R_{16}$, $NR_{17}$, O and S; n is 0 to 3.

Another preferred embodiment is a compound of Formula V:

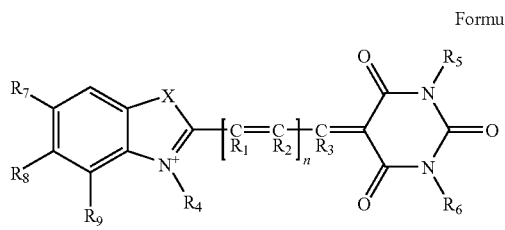

Formula V wherein $R_1$ to $R_{17}$ are hydrogen, alkyl having from 1-20 carbons, alkoxy having from 1-20 carbons, trifluoromethyl, halogen, methylthio, sulfonyl, carbonyl, hydroxy, amino, thiol, RM and LQM; X is $CR_{15}R_{16}$, $NR_{17}$, O and S; n is 0 to 3.

Another preferred embodiment is a compound of Formula VI:

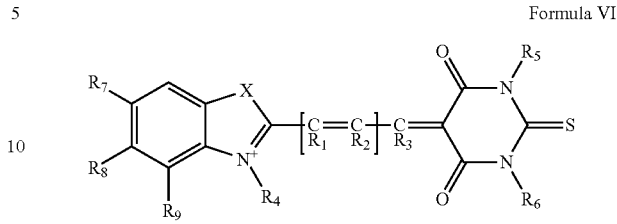

Formula VI wherein $R_1$ to $R_{17}$ are hydrogen, alkyl having from 1-20 carbons, alkoxy having from 1-20 carbons, trifluoromethyl, halogen, methylthio, sulfonyl, carbonyl, hydroxy, amino, thiol, RM and LQM; X is $CR_{15}R_{16}$, $N11_{-17}$, O and S; n is 0 to 3.

The length of the polymethine bridge between the two ring systems greatly affects the dye's absorption and emission properties. Each of $R_1$, $R_2$, $R_3$, when present, is independently H, F, Cl, alkyl having 1-6 carbons, alkoxy having 1-6 carbons, aryloxy, a N-heteroaromatic moiety, or an iminium ion. Alternatively, two substituents $R_1/R_2$, $R_2/R_3$, when taken in combination, form a 4-, 5-, or 6-membered saturated or unsaturated hydrocarbon ring that is unsubstituted or is optionally substituted one or more times by a saturated or unsaturated alkyl having 1-6 carbons, halogen, or a carbonyl oxygen. Examples of appropriate BRIDGE moieties have been previously described in the literature of U.S. Pat. No. 5,831,098 to Ollmann, Jr (1998); U.S. Pat. No. 6,086,737 to Patonay et al. (2000); U.S. Pat. No. 6,048,982 to Waggoner (2000); and U.S. Pat. No. 5,453,505 to Lee et al. (1995); U.S. Pat. No. 5,639,874 to Middendorf et al. (1997); U.S. Pat. No. 3,864,644 to Lincoln et al. (1975); U.S. Pat. No. 4,011,086 to Simson (1977).

Typically, each of $R_1$, $R_2$ and $R_3$, when present, is H. Where one of $R_1$, $R_2$ and $R_3$ is nonhydrogen, it is typically the substituent on the center carbon of BRIDGE. Similarly, where BRIDGE incorporates a 4-, 5-, or 6-membered ring, it typically occurs at the center of the BRIDGE moiety.

Additionally, selection of the X and Y moieties may also significantly affect the dye's absorption and fluorescence emission properties. X and Y are optionally the same or different, and spectral properties of the resulting dye may be tuned by careful selection of X and Y. In one embodiment, X and Y are $CR_{15}R_{16}$, $NR_{17}$, O and S where $R_{15}$ to $R_{17}$ are H or an alkyl group having 1-30 carbons, that is optionally substituted one or more times by hydroxy, carboxy, sulfo, amino, alkylamino having 1-6 carbons or dialkylamino having 2-20 carbons. Alternatively, $R_{15}$ and $R_{16}$ in combination complete a five or six membered saturated or unsaturated ring that is optionally substituted by RM or LQM combines with a methine substituent to form a ring, as described below. Preferably $R_{15}$ and $R_{16}$ are independently alkyl with 1-6 carbon atoms that are unsubstituted or are substituted once by hydroxy, sulfo, carboxy or amino. In one aspect of the invention, $R_{15}$ and $R_{16}$ are alkyls having 1-6 carbons, preferably methyls. In another aspect of the invention, one of $R_{15}$ and $R_{16}$ is methyl, and the other is alkyl having 1-6 carbons that is substituted by carboxy or by sulfo or by hydroxy, or by LQM.

Incorporation of one or more non-hydrogen substituents on the fused rings can be used to fine tune the absorption and emission spectrum of the resulting dye.

A preferred version of the invention is a compound of Formula VII

Formula VII

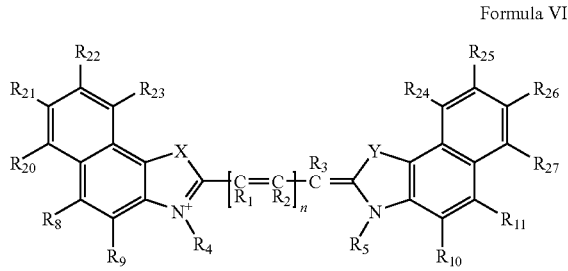

wherein $R_1$ to $R_{27}$ are hydrogen, alkyl having from 1-20 carbons, alkoxy having from 1-20 carbons, trifluoromethyl, halogen, methylthio, sulfonyl, carbonyl, hydroxy, amino, thiol, RM and LQM; X and Y are $CR_{15}R_{16}$, $NR_{17}$, O and S; n is 0 to 3.

A preferred version of the invention is a compound of Formula VIII

Formula VIII

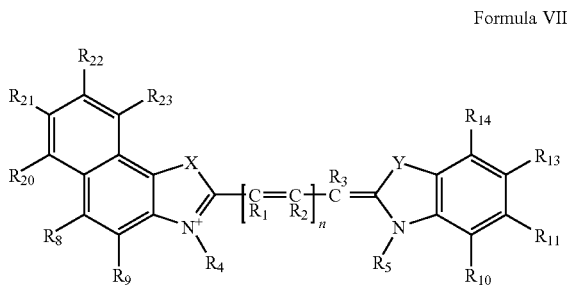

wherein $R_1$ to $R_{23}$ are hydrogen, alkyl having from 1-20 carbons, alkoxy having from 1-20 carbons, trifluoromethyl, halogen, methylthio, sulfonyl, carbonyl, hydroxy, amino, thiol, RM and LQM; X is $CR_{15}R_{16}$, $NR_{17}$, O and S; n is 0 to 3.

In one aspect of the invention, one or two or more of $R_1$ to $R_{27}$ is bromo, iodo and nitro according to Formula I. In one aspect of the invention, the carbocyanine dyes of the invention are sulfonated one or more times.

In addition, the dyes of the invention are substituted by one or more chemically reactive groups (RM) or conjugated substances as described below. In a preferred embodiment, the dye of the invention is substituted by only one RM.

Many embodiments of the compounds of the invention possess an overall electronic charge. It is to be understood that when such electronic charges are shown to be present, they are balanced by the presence of an appropriate counterion, which may or may not be explicitly identified. A biologically compatible counterion, which is preferred for some applications, is not toxic in biological applications, and does not have a substantially deleterious effect on biomolecules. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Where the compound of the invention is negatively charged, the counterion is typically selected from, but not limited to, alkali metal ions, alkaline earth metal ions, transition metal ions, ammonium or substituted ammonium or pyridinium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

It is to be understood that the dyes of the invention have been drawn in one or another particular electronic resonance structure. Every aspect of the instant invention applies equally to dyes that are formally drawn with other permitted resonance structures, as the electronic charge on the subject dyes are delocalized throughout the dye itself.

In one embodiment of the invention, the dye contains at least one L-LQM, where LQM is the luminescence-quenching group that is attached to the dye by a covalent linkage L. In certain embodiments, the covalent linkage attaching the dye to LQM contains multiple intervening atoms that serve as a spacer. The dyes with a LQM label a wide variety of organic or inorganic substances that contain or are modified to contain functional groups with suitable reactivity, resulting in chemical attachment of the conjugated substance. As used herein, "luminescence-quenching group (LQM)" means a heterocyclic moiety on the compound that is capable of quenching the luminescence of 'host chromophore'. Typically LQM is a five- or six-membered heterocycle that has zero to four condensed aromatic rings. LQMs are, but not limited to, thiophene, pyrrole, furan, pyrazole, oxazole, imidazoles, thiazole, triazole, thiadiazole, pyridine, pyridazine, pyrimidine, purine, quinoline, cinnoline, quinoxaline, cabazole, phenanthroline, phenothiazine, acridine, indole, benzoxazole, benzimidazoles, benzothiazole and their variations (for more example see A. R. Katritzky, Comprehensive Heterocyclic Chemistry: The Structure, Reactions, Synthesis, and Uses of Heterocyclic Compounds, 1984, Pergamon). Preferably LQMs are thiophene, pyrrole and purine. More preferably LQM is thiophene.

In one embodiment of the invention, the dye contains at least one L-RM, where RM is the reactive group that is attached to the dye by a covalent linkage L. In certain embodiments, the covalent linkage attaching the dye to RM contains multiple intervening atoms that serve as a spacer. The dyes with a RM label a wide variety of organic or inorganic substances that contain or are modified to contain functional groups with suitable reactivity, resulting in chemical attachment of the conjugated substance. As used herein, "reactive group (RM)" means moiety on the compound that is capable of chemically reacting with a functional group on a different compound to form a covalent linkage. Typically the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the reactive dye and the substance to be conjugated results in one or more atoms of the reactive group RM to be incorporated into a new linkage L attaching the dye to the conjugated substance. Selected examples of reactive groups and linkages are shown in Table 1, where the reaction of an electrophilic group and a nucleophilic group yields a covalent linkage.

TABLE 1

Examples of RM groups to useful covalent linkages.

| Electrophilic Group | Nucleophilic Group | Resulting Conjugate |
|---|---|---|
| Activated esters* | Amines/anilines | Carboxamides |
| Acrylamides | Thiols | Thioethers |
| Acyl azides** | Amines/anilines | Carboxamides |
| Acyl halides | Amines/anilines | Carboxamides |
| Acyl halides | Alcohols/phenols | Esters |
| Acyl nitriles | Amines/anilines | Esters |
| Acyl nitriles | Alcohols/phenols | Carboxamides |
| Aldehydes | Amines/anilines | Imines |
| Aldehydes | Hydrazines | Hydrazones |
| Aldehydes or ketones | Hydrazines | Hydrazones |
| Aldehydes or ketones | Hydroxylamines | Oximes |
| Alkyl halides | Amines/anilines | Alkyl amines |
| Alkyl halides | Carboxylic acids | Esters |
| Alkyl halides | Thiols | Thioethers |
| Alkyl halides | Alcohols/phenols | Ethers |
| Alkyl sulfonates | Thiols | Thioethers |
| Alkyl sulfonates | Carboxylic acids | Esters |
| Alkyl sulfonates | Alcohols/phenols | Ethers |
| Anhydrides | Alcohols/phenols | Esters |
| Anhydrides | Amines/anilines | Carboxamides |
| Aryl halides | Thiols | Thiophenols |
| Aryl halides | Amines | Aryl amines |
| Aziridines | Thiols | Thioethers |
| Boronates | Glycols | Boronate esters |
| Carbodiimides | Carboxylic acids | N-acylureas or anhydrides |
| Diazoalkanes | Carboxylic acids | Esters |
| Epoxides | Thiols | Thioethers |
| Haloacetamides | Thiols | Thioethers |
| Haloplatinate | Amino | Platinum complex |
| Haloplatinate | Heterocycle | Platinum complex |
| Haloplatinate | Thiol | Platinum complex |
| Halotriazines | Amines/anilines | Aminotriazines |
| Halotriazines | Alcohols/phenols | Triazinyl ethers |
| Imido esters | Amines/anilines | Amidines |
| Isocyanates | Amines/anilines | Ureas |
| Isocyanates | Alcohols/phenols | Urethanes |
| Isothiocyanates | Amines/anilines | Thioureas |
| Maleimides | Thiols | Thioethers |
| Phosphoramidites | Alcohols | Phosphate esters |
| Silyl halides | Alcohols | Silyl ethers |
| Sulfonate esters | Amines/anilines | Alkyl amines |
| Sulfonate esters | Thiols | Thioethers |
| Sulfonate esters | Carboxylic acids | Esters |
| Sulfonate esters | Alcohols | Ethers |
| Sulfonyl halides | Amines/anilines | Sulfonamides |
| Sulfonyl halides | Phenols/alcohols | Sulfonate esters |

*Activated esters, as understood in the art, generally have the formula —COW, where W is a good leaving group (e.g. succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOAlk or —OCN(Alk$_1$)NH(Alk$_2$), where Alk$_1$ and Alk$_2$, which may be the same or different, are C$_1$-C$_{20}$ alkyl, C$_1$-C$_{20}$ perfluoroalkyl, or C$_1$-C$_{20}$ alkoxy; or cyclohexyl, 3-dimethylaminopropyl, or N-morpholinoethyl).
**Acyl azides can also rearrange to isocyanates.

Choice of the reactive group used to attach the dye to the substance to be conjugated typically depends on the functional group on the substance to be conjugated and the type or length of covalent linkage desired. The types of functional groups typically present on the organic or inorganic substances include, but are not limited to, amines, amides, thiols, alcohols, phenols, aldehydes, ketones, phosphates, imidazoles, hydrazines, hydroxylamines, disubstituted amines, halides, epoxides, carboxylate esters, sulfonate esters, purines, pyrimidines, carboxylic acids, olefinic bonds, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one dye, which may be the same or different, or to a substance that is additionally modified by a hapten, such as biotin. Although some selectivity can be obtained by careful control of the reaction conditions, selectivity of labeling is best obtained by selection of an appropriate reactive dye.

Typically, RM will react with an amine, a thiol, an alcohol, an aldehyde or a ketone. Preferably RM reacts with an amine or a thiol functional group. In one embodiment, RM is an acrylamide, a reactive amine (including a cadaverine or ethylenediamine), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. Nos. 5,580,990; 5,714,327; 5,985,566.

Where the reactive group is a photoactivatable group, such as an azide, diazirinyl, azidoaryl, or psoralen derivative, the dye becomes chemically reactive only after illumination with light of an appropriate wavelength. Where RM is an activated ester of a carboxylic acid, the reactive dye is particularly useful for preparing dye-conjugates of proteins, nucleotides, oligonucleotides, or haptens. Where RM is a maleimide or haloacetamide the reactive dye is particularly useful for conjugation to thiol-containing substances. Where RM is a hydrazide, the reactive dye is particularly useful for conjugation to periodate-oxidized carbohydrates and glycoproteins, and in addition is an aldehyde-fixable polar tracer for cell microinjection. Preferably, RM is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. More preferably, RM is a succinimidyl ester of a carboxylic acid, a maleimide, an iodoacetamide, or a reactive platinum complex.

Based on the above-mentioned attributes, the appropriate reactive dye of the invention is selected for the preparation of the desired dye-conjugate, whose advantageous properties make them useful for a wide variety of applications. Particularly useful dye-conjugates include, among others, conjugates where substrate is a peptide, nucleotide, antigen, steroid, vitamin, drug, hapten, metabolite, toxin, environmental pollutant, amino acid, protein, nucleic acid, nucleic acid polymer, carbohydrate, lipid, ion-complexing moiety, or glass, plastic or other non-biological polymer. Alternatively, substrate is a cell, cellular system, cellular fragment, or subcellular particle, e.g. inter alia, a virus particle, bacterial particle, virus component, biological cell (such as animal cell, plant cell, bacteria, yeast, or protist), or cellular component. Reactive dyes typically label functional groups at the cell surface, in cell membranes, organelles, or cytoplasm.

Typically substrate is an amino acid, peptide, protein, tyramine, polysaccharide, ion-complexing moiety, nucleoside, nucleotide, oligonucleotide, nucleic acid, hapten, psoralen, drug, hormone, lipid, lipid assembly, polymer, polymeric microparticle, biological cell or virus. More typically, substrate is a peptide, a protein, a nucleotide, an oligonucleotide, or a nucleic acid.

In one embodiment, substrate is a biological polymer such as a peptide, protein, oligonucleotide, or nucleic acid polymer that is also labeled with at least a second luminescent dye (optionally an additional dye of the present invention), to form an energy-transfer pair. In some aspects of the invention, the labeled conjugate functions as an enzyme substrate, and enzymatic hydrolysis disrupts the energy transfer. Alternatively, substrate is itself a fluorescent dye (such as green fluorescent proteins and Phycobiliproteins).

In one embodiment, substrate is an amino acid (including those that are protected or are substituted by phosphates, carbohydrates, or $C_1$ to $C_{25}$ carboxylic acids), or is a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins, chemokines and growth factors. In one preferred aspect, the conjugated protein is a phycobiliprotein, such as allophycocyanin, phycocyanin, phycoerythrin, allophycocyanin B, B-phycoerythrin, phycoerythrocyanin, and b-phycoerythrin (for example, see U.S. Pat. No. 5,714,386 to Roederer (1998)). Particularly preferred are conjugates of R-phycoerythrin and of allophycocyanin with selected dyes of the invention that serve as excited-state energy acceptors or donors. In these conjugates, excited state energy transfer results in long wavelength fluorescence emission when excited at relatively short wavelengths.

In another embodiment, substrate is a nucleic acid base, nucleoside, nucleotide or a nucleic acid polymer, including those that are modified to possess an additional linker or spacer for attachment of the dyes of the invention, such as an alkynyl linkage (U.S. Pat. No. 5,047,519), an aminoallyl linkage (U.S. Pat. No. 4,711,955), or a heteroatom-substituted linker (U.S. Pat. No. 5,684,142) (all patents), or other linkage. In another embodiment, the conjugated substance is a nucleoside or nucleotide analog that links a purine or pyrimidine base to a phosphate or polyphosphate moiety through a non-cyclic spacer. In another embodiment, the dye is conjugated to the carbohydrate portion of a nucleotide or nucleoside, typically through a hydroxyl group but additionally through a thiol or amino group (U.S. Pat. Nos. 5,659,025, 5,668,268, 5,679,785; all). Typically, the conjugated nucleotide is a nucleoside triphosphate or a deoxynucleoside triphosphate or a dideoxynucleoside triphosphate. Incorporation of methylene moieties or nitrogen or sulfur heteroatoms into the phosphate or polyphosphate moiety is also useful. Nonpurine and nonpyrimidine bases such as 7-deazapurines (U.S. Pat. No. 6,150,510, incorporate by reference) and nucleic acids containing such bases can also be coupled to dyes of the invention. Nucleic acid adducts prepared by reaction of depurinated nucleic acids with amine, hydrazide or hydroxylamine derivatives provide an additional means of labeling and detecting nucleic acids, e.g. "A method for detecting abasic sites in living cells: age-dependent changes in base excision repair." Atamna H, Cheung I, Ames B N. Proc Natl Acad Sci U.S. Pat. No. 97,686-691 (2000).

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates, or peptide nucleic acids such as N-(2-aminoethyl)glycine units. When the nucleic acid is a synthetic oligonucleotide, it typically contains fewer than 50 nucleotides, more typically fewer than 25 nucleotides. Conjugates of peptide nucleic acids (PNA) (Nielsen et al U.S. Pat. No. 5,539,082) may be preferred for some applications because of their generally faster hybridization rates.

In one embodiment, the conjugated oligonucleotides of the invention are aptamers for a particular target molecule, such as a metabolite, dye, hapten, or protein. That is, the oligonucleotides have been selected to bind preferentially to the target molecule. Methods of preparing and screening aptamers for a given target molecule have been previously described and are known in the art (for example, U.S. Pat. No. 5,567,588 to Gold (1996)).

In one embodiment, conjugates of biological polymers such as peptides, proteins, oligonucleotides, nucleic acid polymers are also labeled with at least a second luminescent dye, that is optionally an additional dye of the present invention, to form an energy-transfer pair. In some aspects of the invention, the labeled conjugate functions as an enzyme substrate, and enzymatic hydrolysis disrupts the energy transfer. In another embodiment of the invention, the energy-transfer pair that incorporates a dye of the invention is conjugated to an oligonucleotide that displays efficient fluorescence quenching in its hairpin conformation [the so-called "molecular beacons" of Tyagi et al., NATURE BIOTECHNOLOGY 16, 49 (1998)] or fluorescence energy transfer.

The preparation of dye conjugates using reactive dyes is well documented, e.g. by R. Haugland, MOLECULAR PROBES HANDBOOK OF FLUORESCENT PROBES AND RESEARCH CHEMICALS, Chapters 1-3 (1996); and Brinkley, BIOCONJUGATE CHEM., 3, 2 (1992). Conjugates typically result from mixing appropriate reactive dyes and the substance to be conjugated in a suitable solvent in which both are soluble. The majority of the dyes of the invention are readily soluble in aqueous solutions, facilitating conjugation reactions with most biological materials. For those reactive dyes that are photoactivated, conjugation requires illumination of the reaction mixture to activate the reactive dye.

Synthesis

Synthesis of the cyanine dyes of the invention, where attachment is at the 1-position of the indolium, oxazolium, thiazolium and imidazolium, depends on initial preparation of certain key intermediates. The intermediates have the following general structure (for simplicity, all but a few of the possible substituents are shown as hydrogen):

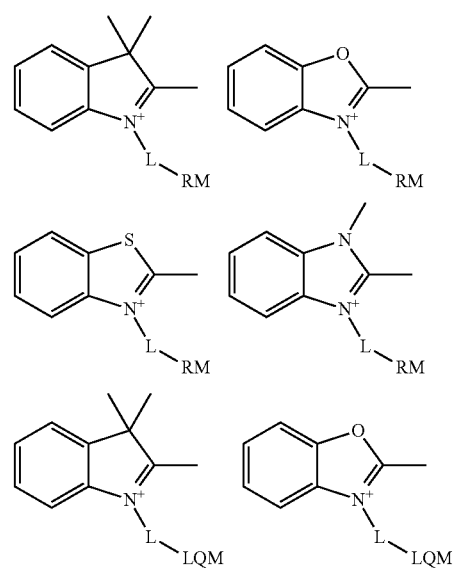

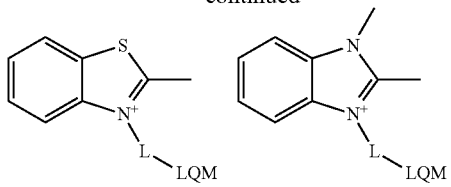

These basic structures are optionally further substituted, during or after synthesis, to give the corresponding dye substituents as defined above. For carbocyanines, the novel key intermediates are readily synthesized by a reaction that is analogous to a Fischer indole synthesis (see R. J. Sundberg, The chemistry of indoles, Organic chemistry, a series of monographs, 1970, Academic Press). For imidazoles, oxazoles and thioxazoles, the intermediates are readily prepared from the condensations of 2-substituted anilines with a carbonyl compound [D. C. Palmer, The Chemistry of Heterocyclic Compounds, Oxazoles: Synthesis, Reactions, and Spectroscopy, Part B (Chemistry of Heterocyclic Compounds: A Series of Monographs, 2004, Wiley-Interscience)]. The typical total synthesis of 1-RM- and 1-LQM-substituted carbocyanines is illustrated in FIGS. 1 and 4.

Synthesis of the cyanine dyes of the invention, where attachment is at the 3-position of the indolium and imidazolium, depends on initial preparation of certain key intermediates. The intermediates have the following general structure (for simplicity, all but a few of the possible substituents are shown as hydrogen). These basic structures are optionally further substituted, during or after synthesis, to give the corresponding dye substituents as defined above. The novel key intermediates are readily synthesized by a reaction that is analogous to a Fischer indole synthesis or through the condensations of phenylendiamine with a carbonyl compound. The typical total synthesis of 3-RM-and 3-LQM-substituted carbocyanines is illustrated in FIGS. 2 and 5.

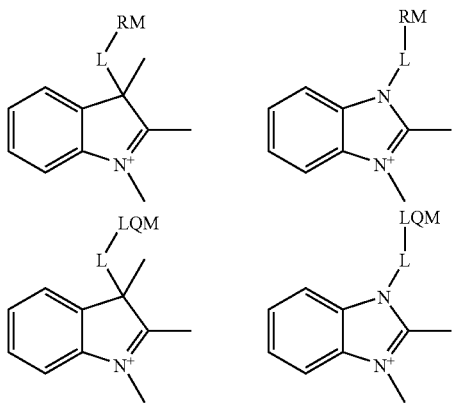

Synthesis of the cyanine dyes of the invention, where attachment is at the bridged double bonds, depends on initial preparation of certain key BRIDGE intermediates. For example, N,N'-diphenylformamidine and triethylorthoformate malonaldehyde bis(phenylimine) hydrochloride, 1,1,3-trimethoxypropane, and 1,1,3,3-tetramethoxypropane, and glutaconaldehyde dianil monochloride are the well-known the BRIDGE intermediates used in the synthesis of carbocyanines. More examples of appropriate BRIDGE moieties have been previously described in the literature of U.S. Pat. No. 5,831,098 to Ollmann, Jr (1998); U.S. Pat. No. 6,086,737 to Patonay et al. (2000); U.S. Pat. No. 6,048,982 to Waggoner (2000); and U.S. Pat. No. 5,453,505 to Lee et al. (1995); U.S. Pat. No. 5,639,874 to Middendorf et al. (1997); U.S. Pat. No. 3,864,644 to Lincoln et al. (1975); U.S. Pat. No. 4,011,086 to Simson (1977). Typically, each of $R_1$, $R_2$ and $R_3$ in Formula I, when present, is H. Where one of $R_1$, $R_2$ and $R_3$ is nonhydrogen, it is typically the substituent on the center carbon of BRIDGE. Similarly, where BRIDGE incorporates a 4-, 5-, or 6-membered ring, it typically occurs at the center of the BRIDGE moiety. The typical total synthesis of carbocyanines substituted at the BRIDGE atoms with RM/LQM is illustrated in FIGS. 3 and 6.

For the synthesis of carbocyanines, an appropriately substituted aryl hydrazine (for simplicity, all but a few of the possible substituents are shown as hydrogen), which is typically a phenylhydrazine of an appropriately substituted naphthyl hydrazine, is reacted with an appropriately substituted methyl ketone to yield a 3,3-disubstituted 2-methylindole derivative. It is particularly suitable to utilize a sulfonated phenylhydrazine derivative or a sulfonated naphthylhydrazine derivative to increase the solubility of the final dye. The 3,3-disubstituted-2-methylindole is then quaternized on the nitrogen atom to an indolium derivative with an alkylating agent that is typically an alkyl halide such as ethyl iodide, an alkylsulfonate such as methyl p-toluenesulfonate or a cyclic sulfonate such as propanesultone or butanesultone. Typically, the key indolium or benzoindolium intermediates are sulfonated one or more times before or after quaternization and subsequent condensation with the benzazolium moiety and polymethine moiety to form the subject dyes. Variations on these methods are well known in the art that yield substituents on the polymethine bridge or on the indolium or benzolium portion of the dye precursor.

Scheme 1. Typical synthesis of indolium intermediates

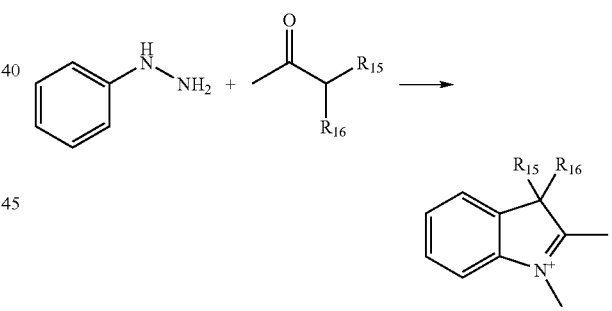

The azacarbocyanine dyes of the present invention can be analogously syntheiszed. (see, for example, Brooker, et al., J. AM. CHEM. SOC., 64, 199 (1942); Heravi, et al., INDIAN J. CHEM. 36B, 1025 (1997); Smith et al. SULFUR LETTERS 17, 197 (1994); Chu-Moyer et al. J. ORG. CHEM. 60, 5721 (1995); Turner, J. ORG. CHEM. 48, 3401 (1983); Couture et al. J. HETEROCYCLIC CHEM. 24, 1765 (1987); Petric et al. J. HETEROCYCLIC CHEM. 14, 1045, (1977); Barlin et al. AUST. J. CHEM., 37, 1729 (1984); Saikachi et al. CHEM. & PHARM. BULL. 9, 941 (1961); Barlin AUST. J. CHEM. 36, 983 (1983); Foye et al., J. PHARM. SCI. 64, 1371 (1975); Khanna et al. J. ORG. CHEM. 60, 960 (1995)); British Patent No. 870,753 to Ficken et al. (1961); Ficken et al., "Diazaindenes and Their Quaternary Salts—Part I" pp 3202-3212 (1959); Ficken et al., "Diazaindenes and Their Quaternary Salts—Part II" pp 584-588 (1961). In general, the synthesis of these dyes requires three precursors: the appropriate benzazolium or azabenzazolium salt (the "A" and "B" moieties), and a source for the polymethine spacer. Typically each component is selected so as to incorporate the appropriate chemical substituents, or functional groups (e.g. LQM and RM) that can be converted to the appropriate substituents. The chemistry that is required to prepare and combine these precursors so as to yield any of the subject derivatives is generally well understood by one skilled in the art.

It is recognized that there are many possible variations that may yield an equivalent results. The substituents on the aromatic carbons of the azabenzazolium moiety are typically incorporated in the parent aza- or polyazabenzazole molecule prior to quaternization with an alkylating agent. However, such substituents may also be incorporated during the synthesis of the azabenzazole moiety. Alkyl, alkoxy, carboxyl, and halogen substituents at aromatic carbons are typically already present as substituents on the benzazole or azabenzazole precursors, or on compounds that are readily converted to such precursors using methods well-known in the art. Sulfonic acid groups are typically introduced on the precursors prior to condensation of the cyanine dye [for example, see U.S. Pat. No. 5,767,287 to Bobrow et al. (1998)]. Aminoalkyl groups are typically substituted by a protecting group when they are first introduced, typically by substitution onto the benzazole or azabenzazole precursor. The protecting group is then removed after condensation of the cyanine dye. Aromatic amino groups are typically prepared via the reduction of a nitro substituted benzazolium precursor, which in turn is prepared by the nitration of the benzazole precursor.

The dye molecules that have LQM directly conjugated with Ring A (in Formula I) are synthesized from the aromatic heterocycle-substitued indolium, oxazolium, thiazolium and imidazolium intermediates prepared from Suzuki coupling (or equivalent reactions) as illustrated below.

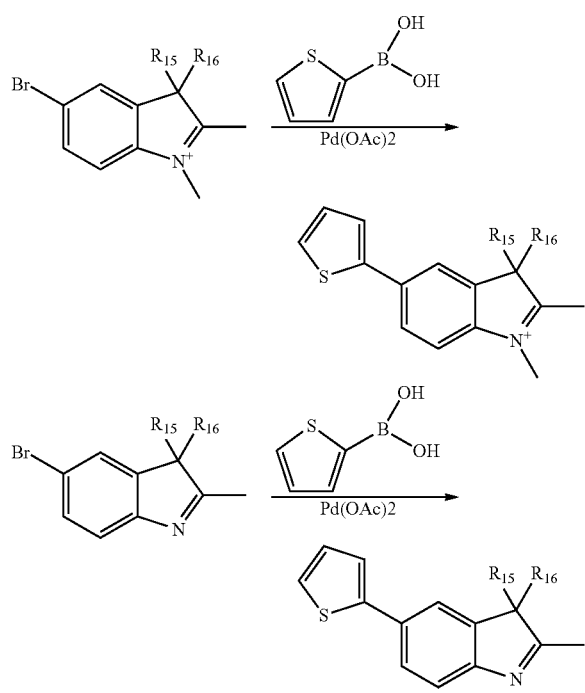

Scheme 2. Typical synthesis of heterocycle-conjugated indolium intermediates

The methods for synthesis of dyes that contain a variety of reactive groups such as those described in Table 1 are well documented in the art. Particularly useful are amine-reactive dyes such as "activated esters" of carboxylic acids, which are typically synthesized by coupling a carboxylic acid to a relatively acidic "leaving group". Other preferred amine-reactive groups include sulfonyl halides, which are prepared from sulfonic acids using a halogenating agent such as $PCl_5$ or $POCl_3$; halotriazines, which are prepared by the reaction of cyanuric halides with amines; and isothiocyanates or isothiocyanates, which are prepared from amines and phosgene or thiophosgene, respectively.

Dyes containing amines and hydrazides are particularly useful for conjugation to carboxylic acids, aldehydes and ketones. Most often these are synthesized by reaction of an activated ester of a carboxylic acid or a sulfonyl halide with a diamine, such as cadaverine, or with a hydrazine. Alternatively, aromatic amines are commonly synthesized by chemical reduction of a nitroaromatic compound Amines and hydrazines are particularly useful precursors for synthesis of thiol-reactive haloacetamides or maleimides by standard methods.

Nucleosides and nucleotides labeled with dyes of the invention are particularly useful for some applications of nucleic acid labeling. The use of carbocyanine-amidites for labeling nucleotides and nucleosides have been previously described [U.S. Pat. No. 5,986,086 to Bruch et al. (1999); U.S. Pat. No. 5,808,044 to Brush et al. (1998); U.S. Pat. No. 5,556,959 to Brush et al. (1996)].

Examples of some synthetic strategies for selected dyes of the invention, as well as their characterization, synthetic precursors, conjugates and method of use are provided in the examples below. Further modifications and permutations will be obvious to one skilled in the art.

Applications and Methods of Use

The term "quenching compound" is used herein to refer to all aspects of the claimed quenching cyanines, including styryl dyes. In one aspect of the invention, the quenching compounds of the invention are useful simply as calorimetric labels for a conjugated substance. The compounds of the invention typically have large extinction coefficients, and thereby permit the detection of the quenching compound-conjugated substance by virtue of the visible light absorption of the quenching compound.

The quenching compounds of the present invention accept energy from a wide variety of luminophores, provided that the quenching compound and the luminophore are in sufficiently close proximity for quenching to occur, and that at least some spectral overlap occurs between the emission wavelengths of the luminophore and the absorption band of the quenching compound. This overlap may occur with emission of the donor occurring at a lower or even higher wavelength emission maximum than the maximal absorbance wavelength of the quenching compound, provided that sufficient spectral overlap exists. Energy transfer may also occur through transfer of emission of the donor to higher electronic states of the acceptor, such as from tryptophan residues of proteins to the weaker absorption bands between 300 and 350 nm typical of the dyes in the ultraviolet region. Preferably, the quenching compound of the invention is only dimly fluorescent, or essentially nonfluorescent, so that energy transfer results in little or no fluorescence emission. In one aspect of the invention, the quenching compound of the invention has a fluorescence quantum yield of less than about 0.1. In another aspect of the invention, the quenching compound of the invention has a fluorescence quantum yield of less than about 0.05. In yet another aspect of the invention, the quenching compound of the invention has a fluorescence quantum yield of less than about 0.01.

Typically, quenching occurs through Fluorescence Resonance Energy Transfer between a donor and a quenching acceptor of the invention. The degree of FRET exhibited by a donor acceptor pair can be represented by the equations [1] to [3]:

The efficiency (E %) and rate ($k_T$) of FRET are respectively expressed as follows:

$$E\% = k_T/(\tau_D^{-1} + k_T) \quad [1]$$

$$k_T = R_o^6 \gamma^{-6} \tau_D^{-1} \quad [2]$$

Where $\tau_D$ is the decay time of the donor in the absence of acceptor; $\gamma$ is the donor-acceptor (D-A) distance; $R_o$ is the Förster distance where FRET has 50% efficiency, is typically in the range of 20-60 Å. $R_o$ is determined by the following equation:

$$R_o^6 = 8.79 \times 10^{23} [k^2 n^{-4} \Phi_D J(\lambda)] \quad [3]$$

Where $k^2$ is dipole-dipole orientation factor (ranging from 0 to 4, $k^2 = 2/3$ for randomly oriented donors and acceptors); n is refractive index [The refractive index is generally known from solvent composition or estimated for macromolecules such as proteins and nucleic acids. n is often assumed to be that of water (n=1.33) for aqueous solutions, or to be that of small molecules (n=1.39) for organic solutions]. $\Phi_D$ is the fluorescence quantum yield of donor in the absence of acceptor. $J(\lambda)$ is FRET spectral overlap integral as illustrate in FIG. 2.2, and is determined by the following equation:

$$J(\lambda) = \int F_D(\lambda) \epsilon_A(\lambda) \lambda^4 d(\lambda) \quad [4]$$

Where $F_D(\lambda)$ is the corrected fluorescence intensity of the donor in the wavelength range $\lambda$ to $\lambda + \Delta\lambda$ with the total intensity (area under the curve) normalized unity; $\epsilon_A$ is extinction coefficient of the acceptor at $\lambda$.

Scheme 3. Schematic representation of the FRET spectral overlap integral.

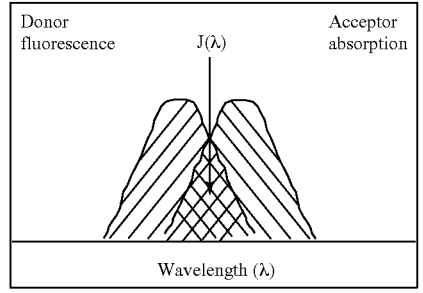

From the above equations, it is easily concluded that an efficient FRET should have the following conditions:
- Distance between donor and acceptor: Donor and acceptor molecules must be in close proximity (typically 10-100 Å).
- Spectral overlap: The absorption spectrum of the acceptor must overlap fluorescence emission spectrum of the donor (see FIG. 2.2).
- Dipole orientation: Donor and acceptor transition dipole orientations must be approximately parallel It should be readily appreciated that the degree of energy transfer during FRET, and therefore quenching, is highly dependent upon the separation distance between the luminophore and the quenching compound. In molecular systems, a change in luminescence quenching typically correlates well with a change in the separation distance between the luminophore molecules and the quenching compound molecules. Assays that detect such changes in luminescence are therefore useful for the detection of a great many structural changes, such as changes in molecular conformation, assembly of structures, or degradation of structures.

Any luminophore with sufficient spectral overlap with a quenching compound of the instant invention, as calculated above, is a suitable donor for the applications of the invention, other factors being equal. The greater the degree of overlap, the greater the overall quenching observed. While fluorescent dyes are preferred for energy transfer applications, any emission that generates light having sufficient spectral overlap with the quenching compounds of the invention is also useful, such as chemiluminescence, or phosphorescence, whether by FRET or by triplet state to singlet state transfer.

While FRET is the most common mechanism for quenching of fluorescence to occur, any combination of molecular orientation and spectral coincidence that results in quenching of luminescence is a useful mechanism for quenching by the quenching compounds of the invention, as described herein. For example, efficient quenching can occur even in the absence of spectral overlap if the luminophore and the quenching compound are sufficiently close together to form a ground-state complex (as described in Tyagi et al., NATURE BIOTECHNOLOGY 16, 49 (1998)).

Typically, where the luminophore is a fluorophore, it is a fluorescent aromatic or heteroaromatic compound that is a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated derivatives thereof [as described in U.S. Pat. No. 5,830,912 to Gee et al. (1998)], a polyazaindacene [such as 4-bora-3a,4a-diaza-s-indacene as described in U.S. Pat. No. 4,774,339 to Haugland, et al. (1988); U.S. Pat. No. 5,187,288 to Kang, et al. (1993); U.S. Pat. No. 5,248,782 to Haugland, et al. (1993); U.S. Pat. No. 5,274,113 to Kang, et al. (1993); and U.S. Pat. No. 5,433,896 to Kang, et al. (1995)], a cyanine, an oxazine or a benzoxazine, a carbazine [U.S. Pat. No. 4,810,636 to Corey (1989)], or a phenalenone or benzphenalenone [U.S. Pat. No. 4,812,409 to Babb et al. (1989)]. The donor dye is optionally an organic molecule that is a fluorophore, or a fluorescent protein such as a phycobiliprotein or "green fluorescent protein". Preferably, the donor dye is a carbazine, an oxazine, a coumarin, a pyrene, a cyanine, a naphthalene, a phenalenone, or a 4-bora-3a,4a-diaza-s-indacene. As used herein, oxazines include resorufins, aminooxazinones, diaminooxazines, and their benzo-substituted analogs. Preferred chemiluminescent dyes include luminol, isoluminol, luciferin, an acridinium ester, or a dioxetane.

Where the synthetic dye is a cyanine [U.S. Pat. No. 6,048,982 (2000); U.S. Pat. No. 6,133,445 (2001) and U.S. Pat. No. 6,686,145 (2004) to Waggoner et al], the synthetic dye is optionally a fluorescein, a rhodol [U.S. Pat. No. 5,227,487 to Haugland, et al. (1993)], or a rhodamine. As used herein, fluorescein includes benzo- or dibenzofluoresceins, seminaphthofluoresceins, or naphthofluoresceins. Similarly, as used herein rhodol includes seminaphthorhodafluors [U.S. Pat. No. 4,945,171 to Haugland, et al. (1990)]. Sulfonated pyrenes, coumarins, carbocyanines, and cyanine dyes have been described previously [U.S. Pat. No. 5,132,432 to Haugland et al., (1992); U.S. Pat. No. 5,696,157 to Wang et al. (1997); U.S. Pat. No. 5,268,486 to Waggoner et al. (1993)].

The quenching compounds of the invention are useful in any application where energy transfer from a luminescent donor to a non-fluorescent acceptor has previously been described, provided that some spectral overlap exists between the emission of the donor dye and the absorbance of the quenching compound of the invention. Typically, the quenching compounds are used in combination with a luminophore in a method that detects a change in separation distance between the luminophore and the quenching compound.

The donor luminophores and quenching compounds used in the instant methods are useful in any medium in which they are sufficiently soluble. For example, selected embodiments of the instant quenching compounds that are substituted by highly non-polar substituents may be useful in organic solvents, or on or in non-polar matrices, such as polymeric microspheres. For biological applications, the quenching compounds of the invention and their conjugates are typically used in an aqueous, mostly aqueous or aqueous-miscible solution prepared according to methods generally known in the art.

Chemically reactive compounds of the invention will covalently attach to a corresponding functional group on a wide variety of materials, forming conjugates as described above. Photoreactive compounds of the invention can be used similarly to photolabel nucleic acids, or components of the outer membrane of biological cells, or as photo-fixable polar tracers for cells.

The quenching compounds of the invention are generally utilized by labeling a substance or sample of interest under conditions selected so that illumination of the sample with an appropriate wavelength of light results in a detectable optical response. In one embodiment, the quenching compounds of the invention are utilized as calorimetric labels, such that the detectable optical response is an absorption of illumination energy. In another embodiment the quenching compound accepts energy from a donor, such that the detectable optical response is quenching of the luminescence of the donor.

In most applications of the instant compounds, the labeled substance is utilized in a homogenous solution assay, where specific spatial resolution is not required. In these embodiments of the invention the loss of, or restoration of, luminescence in the sample is detected. In another embodiment, the quenching compound forms a covalent or non-covalent association or complex with an element of the sample where a luminescent component is present or is subsequently added. In this embodiment, illumination of the sample reveals either a luminescence response if quenching is not occurring, or the degree of quenching may be observed and correlated with a characteristic of the sample. Such correlation typically occurs by comparison with a standard or a calibration curve. Typically, a stained sample is illuminated and observed in order to determine a specified characteristic of the sample by comparing the degree of quenching exhibited to a luminescence standard of determined intensity. The luminescence standard may be a fluorescent dye such as the fluorophore used to prepare the quenching compound-fluorophore labeled substance, a luminescent particle (including fluorescent microspheres), a calibration curve prepared by assaying the doubly labeled substance with a known amount of enzyme or degradation activity, or any other standard that can be used to calibrate luminescence signal intensity as well known in the art.

Typically, the method of the invention comprises the steps of
a) illuminating the molecular system under study;
b) detecting the luminescence response of the system, which yields information as to the separation distance one or more luminophore donors and quenching compound acceptors;
c) exposing the molecular system to an environmental condition sufficient to change the separation distance, or thought to be sufficient to change the separation distance;
d) illuminating the molecular system again;
e) detecting the luminescence response of the molecular system again; and
f) comparing the first detected luminescence response to the second detected luminescence response, in order to determine a detectable difference in the detected luminescence before and after the exposure to the selected environmental condition. The detected change in the luminescence of the molecular system then correlates with any changes that occurred in the separation distance between the luminophores and the quenching compounds, typically in response to the selected environmental condition.

As discussed in greater detail below, the environmental condition of the instant method may be the presence of a particular enzyme, the presence of a complementary specific binding pair member, a change in pH, or a change in sample temperature.

Illumination and Detection

Typically, changes in luminescence quenching are detected by methods well known in the art for standard luminescence assays. Sample luminescence, if present, is typically detected by illumination of the sample with a light source capable of producing light that is absorbed at or near the wavelength of maximum absorption of the donor dye, and luminescence is detected at a wavelength longer than the excitation wavelength, typically near the emission maximum. Such illumination sources include, but are not limited to, hand-held ultraviolet lamps, mercury-arc lamps, xenon lamps, lasers and laser diodes. These illumination sources are optionally integrated into laser scanners, fluorescence microplate readers, standard or minifluorometers, or chromatographic detectors.

The optical response is optionally detected by visual inspection, or by use of instrumentation, including CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal, such as photomultiplier tubes. Where the sample is examined using a flow cytometer, examination of the sample optionally includes sorting portions of the sample according to their luminescence response.

In the case of a sample in which the labeled substance is immobilized or partially immobilized on a solid or semi-solid support or in a matrix such as agar, sample luminescence is typically detected using a transilluminator, an epi-illuminator, a laser scanner, a microscope or a similar apparatus that permits observation of the matrix.

Luminescence occurring within a cell is typically detected using instrumentation that is capable of detecting luminescent emission in single cells, such as a microscope or a flow cytometer (optionally further being followed by sorting of luminescent cells). Alternatively, multiple cells are suspended and luminescence changes are measured as for an assay done in true solution.

As described above, the method of the instant invention is typically useful for detection of changes in separation distance between a luminophore donor and a quenching compound acceptor.

Any assay that relies upon the measurement of the proximity of luminophores and quenching compounds in a system may be carried out using the method of the instant invention. The method of the instant invention is typically utilized to detect and/or quantify the convergence or divergence of the luminophore donor and quenching compound acceptor. By convergence is meant a decrease in the average separation distance between the luminophore and the quenching compound. By divergence is meant an increase in the average separation distance between the luminophore and the quenching compound.

In one embodiment, the method of the instant invention is utilized to detect molecular or structural assembly (convergence). In another embodiment, the method of the invention is utilized to detect molecular or structural disassembly (divergence). In yet another embodiment, the method of the invention is utilized to detect a conformation change in a molecule, macromolecule or structure (optionally convergence or divergence). In yet another embodiment, the method of the instant invention incorporates aspects of the detection of assembly, disassembly, and/or conformation changes.

Detection of Structural Assembly

In one embodiment, the luminescence of a luminophore becomes quenched upon being placed in close proximity to a quenching compound of the invention (thereby decreasing the separation distance). The following systems, among others, can be analyzed using energy transfer pairs to detect and/or quantify structural assembly by measuring convergence of the donor and acceptor:

a) protein subunit assembly
b) enzyme-mediated protein assembly
c) molecular dimensions of proteins
d) membrane-protein interactions
e) protein-protein interactions
f) protein-protein-nucleic acid complex assembly
g) receptor/ligand interactions
h) immunoassays
i) nucleic acid hybridization
j) quantitative detection of specific DNA sequence amplification
k) detection of dna duplex winding
l) nucleic acid-protein interactions
m) nucleic acid-drug interactions
n) primer extension assays for mutation detection
o) reverse transcriptase assay
p) strand exchange in dna recombination reactions
q) membrane fusion assays
r) transmembrane potential sensing
s) ligation assays
t) In particular, specific binding pair members labeled with a quenching compound are typically used as probes for the complementary member of that specific binding pair, by methods well known in the art. The complementary member is typically labeled with a luminescent label, and association of the two members of the specific binding pair results in luminescence quenching. This assay is particularly useful in nucleic acid hybridization assays, evaluation of protein-nucleic acid interaction, and in selected standard immunoassays. In one embodiment, a loss of luminescence indicates the association of an enzyme with an enzyme substrate, agonist or antagonist, such that the luminophore on one is brought into close proximity to a quenching compound on the other. Selected preferred specific binding pair members are proteins that bind non-covalently to low molecular weight ligands (including biotin), oligonucleotides, and drug-haptens. Representative specific binding pairs are shown in Table 2.

TABLE 2

Representative Specific Binding Pairs

| Antigen | Antibody |
|---|---|
| Biotin | Avidin, streptavidin, anti-biotin |
| Folate | Folate-binding protein |
| IgG* | Protein A or protein G |
| Drug | Drug receptor |
| Toxin | Toxin receptor |
| Carbohydrate | Lectin or carbohydrate receptor |
| Peptide | Peptide receptor |
| Protein | Protein receptor |
| Peptide nucleic acid | Complementary strand |
| Enzyme substrate | Enzyme |
| DNA (RNA) | cDNA (cRNA) |
| Hormone | Hormone receptor |
| Ion | Chelator |

*IgG is an immunoglobulin
cDNA and cRNA are complementary strands used for hybridization Alternatively, a monomer, labeled with a quenching compound, is incorporated into a polymer labeled with a luminophore, resulting in quenching of luminescence. In particular, a quenching compound-labeled nucleotide can be incorporated via the polymerase chain reaction into a double stranded DNA molecular that is labeled with a luminophore.

Detection of Structural Disassembly

In another embodiment of the method of the invention, the disassembly, cleavage or other degradation of a molecular structure is detected by observing the partial or complete restoration of luminescence of a luminophore donor. Typically, the initially quenched luminescence of a luminophore associated with the structure becomes dequenched upon being released from the constraint of being in close proximity to a quenching compound of the invention. The quenching compound is optionally associated with the same molecular structure as the luminophore, or the donor and acceptor are associated with adjacent but distinct subunits of the structure. The following systems, among others, can be analyzed using energy transfer pairs to detect and/or quantify structural disassembly:

a) detection of protease activity using fluorogenic substrates (for example HIV protease assays);
b) detection of enzyme-mediated protein modification (e.g. cleavage of carbohydrates/fatty acids, phosphates, prosthetic groups);
c) immunoassays (via displacement/competitive assays);
d) detection of DNA duplex unwinding (e.g. helicase/topoisomerase/gyrase assays);
e) nucleic acid strand displacement;
f) dsDNA melting
g) nuclease activity
h) lipid distribution and transport
i) TAQMAN assays Structure disassembly is typically detected by observing the partial or complete restoration of luminescence, as a conjugated substance is exposed to a degradation conditions of interest for a period of time sufficient for degradation to occur. A restoration of luminescence indicates an increase in separation distance between the luminophore and quenching compound, and therefore a degradation of the conjugated substance. If the detectable difference in luminescence is detected as the degradation proceeds, the assay is a continuous assay. Since most enzymes show some selectivity among substrates, and as that selectivity can be demonstrated by determining the kinetic differences in their hydrolytic rates, rapid testing for the presence and activity of the target enzyme is provided by the enhancement of luminescence of the labeled substrate following separation from the quenching compound.

In another embodiment of the invention, a single-stranded oligonucleotide signal primer is labeled with both a quenching compound and a fluorescent donor dye, and incorporates a restriction endonuclease recognition site located between the donor dye and the quenching compound. The single-stranded oligonucleotide is not cleavable by a restriction endonuclease enzyme, but upon binding to a complementary (target) nucleic acid, the resulting double stranded nucleic acid is cleaved by the enzyme and d the decreased quenching is used to detect the presence of the complementary nucleic acid [U.S. Pat. No. 5,846,726 to Nadeau et al., (1998)].

A single nucleotide polymorphism (SNP) can be detected through the use of sequence specific primers, by detection of melt temperatures of the double stranded nucleic acid. In this aspect, the complementary or substantially complementary strands are labeled with a quenching compound and a luminophore donor, respectively, and dissociation of the two strands (melting) is detected by the restoration of luminescence of the donor.

In yet another example of a divergence assay, the rupture of a vesicle containing a highly concentrated solution of luminophores and quenching compounds is readily detected by the restoration of luminescence after the vesicle contents have been diluted sufficiently to minimize quenching.

Detection of Conformation Changes

In this embodiment, the quenching compound and the fluorescent donor are present on the same or different substances, and a change in the three-dimensional structural conformation of one or more components of the assay results in either luminescence quenching or restoration of luminescence, typically by substantially decreasing or increasing the separation distance between the quenching compound and a luminophore. The following systems, among others, can be analyzed using energy transfer pairs to detect and/or quantify conformation changes:

a) protein conformational changes;
b) protein folding;
c) structure and conformation of nucleic acids;
d) drug delivery;
e) antisense oligonucleotides;
f) cell-cell fusion (e.g. via the diffusion apart of an initial donor-quenching compound pair).

By conformation change is meant, for example, a change in conformation for an oligonucleotide upon binding to a complementary nucleic acid strand. In one such assay, labeled oligonucleotides are substantially quenched when in solution, but upon binding to a complementary strand of nucleic acid become highly fluorescent [so-called "Molecular Beacons", as described in European patent application EP 0 745 690, by Tyagi et al (1996)]. Another example detects the change in conformation when an oligonucleotide that has been labeled at its ends with a quenching compound and a luminophore, respectively, loses its G-quartet conformation upon hybridization to a complementary sequence, resulting in decreased luminescence quenching [U.S. Pat. No. 5,691, 145 to Pitner et al. (1997)]. Alternatively, the binding of an enzyme substrate within the active site of a labeled enzyme may result in a change in tertiary or quaternary structure of the enzyme, with restoration or quenching of luminescence.

Additional Detection Reagents and Assay Kits

When used in complex systems, especially in biological cells, the assays of the instant invention are optionally combined with the use of one or more additional detection reagents, such as an antibody, or a stain for another component of the system such as a nucleic acid stain, an organelle stain, a metal ion indicator, or a probe to assess viability of the cell. The additional detection reagent is optionally a fluorescent reagent exhibiting a color that contrasts with the donor dye present in the assay, or is a label that is detectable by other optical or non-optical properties.

One aspect of the instant invention is the formulation of kits that facilitate the practice of the methods of the invention, as described above. The kit of the invention comprises a quenching compound of the invention, or colorless quenching compound precursor of the invention, typically present conjugated to a nucleotide, oligonucleotide, nucleic acid polymer, peptide, or protein. Typically, the kit further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention.

In one embodiment, the kit comprises a quenching compound of the invention and a luminescent donor. The quenching compound and luminescent donor are optionally each attached to a conjugated substance, or present in solution as free compounds. Such a kit would be useful for the detection of cell-cell fusion, as fusion of a cell containing the quenching compound with a cell containing a luminescent donor would result in quenching of luminescence. Conjugation of either the quenching compound or the luminescent donor or both to biomolecules, such as polysaccharides, would help retain the reagents in their respective cells until cell fusion occurred.

In another embodiment, the kit comprises a quenching compound and a luminescent donor, each conjugated to a complementary member of a specific binding pair. In this aspect of the invention, binding of the two specific binding pair members results in quenching of luminescence, and the kit is useful for the detection of competitive binding to one or the other specific binding pair members, or for the detection of an environmental condition or component that either facilitates or inhibits binding of the specific binding pair members.

In another embodiment, the kit comprises a conjugate of a quenching compound and a conjugate of a luminescent donor, wherein the conjugates are selected such that the action of a particular enzyme results in covalent or noncovalent association of the two conjugates, resulting in quenching of fluorescence. Where the conjugated substances are nucleotides, oligonucleotides or nucleic acid polymers, the kit is useful for the detection of, for example, ligase, telomerase, helicase, topoisomerase, gyrase, DNA/RNA polymerase, or reverse transcriptase enzymes.

In another embodiment, the kit comprises a biomolecule that is covalently labeled by both a quenching compound of the invention and a luminescent donor. In one aspect, the labeled biomolecule exhibits luminescence until a specified environmental condition (such as the presence of a complementary specific binding pair) causes a conformation change in the biomolecule, resulting in the quenching of luminescence. Alternatively, the biomolecule is initially quenched, and a specified environmental condition (such as the presence of an appropriate enzyme or chemical compound) results in degradation of the biomolecule and restoration of luminescence. Such a kit would be useful for the detection of complementary oligonucleotide sequences (as for MOLECULAR BEACONS™), or for the detection of enzymes such as nuclease, lipase, protease, or cellulase.

The examples below are given so as to illustrate the practice of this invention. They are not intended to limit or define the entire scope of this invention.

EXAMPLE 1

Preparation of Compound 1

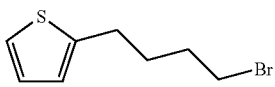

Compound 1

To a solution of thiophene (50 g, 594 mmol) in anhydrous THF (200 mL) is added slowly a 1.6M solution of n-butyllithium in hexane (408 mL, 653 mmol) under nitrogen atomospere at −30° C. The reaction mixture is stirred for a further 2 hours, during which period it is allowed to warm to room temperature. The solution is recooled to 0° C. and a solution of 1,4-dibromobutane (141 g, 653 mmol) in anhydrous THF (100 mL) is added. The stirring is continued overnight. The mixture is diluted with ethyl acetate (1000 mL) and shaken with water (800 mL). The organic layer is washed with brine twice and dried over anhydrous $Na_2SO_4$. After removal of the solvent, the residue is distilled in vacuo to afford 2-(4-bromobutyl)-thiophene 1 as colorless oil (66 g).

EXAMPLE 2

Preparation of Compound 2

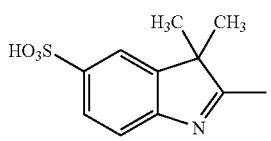

Compound 2

The potassium salt of 2,3,3-trimetylindolenium-5-sulfonate 2 is synthesized by Fisher indole synthesis through the reaction of 4-hydrazinobenzenesulfonic acid and 3-methyl-2-butanone, followed by treatment the sulfonic acid with a saturated solution of potassium hydroxide in 2-propanol.

EXAMPLE 3

Preparation of Compound 3

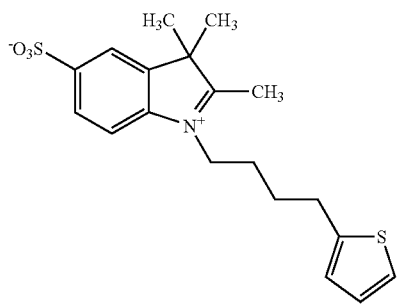

Compound 3

The mixture of the potassium salt of 2,3,3-trimetylindolenium-5-sulfonate 2 (7.5 g, 54.1 mmol) and 2-(4-bromobutyl)-thiophene 1 (11.9 g, 54 1 mmol) in dichlorobenzene (6 mL) is heated at 120° C. for 10 hours under nitrogen. The crude product is triturated with 2-propanol. The solid is filtered and washed with 2-propanol and ether and dried under vacuum to give Compound 3 (10.0 g, 98%).

EXAMPLE 4

Preparation of Compound 4

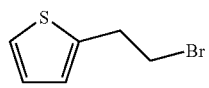

Compound 4

To a solution of 2-(2-thienyl)ethanol (9.5 g 74 mmol) in cabon tetrachloride (30 mL) is added phosphorus tribromide (21.65 g, 80 mmol) quickly at 60° C. The mixture is kept at 65° C. for 20 min. After cooling to room temperature, the mixture is treated with water. The organic layer is washed with sat'd $NaHCO_3$ and brine and dried over $Na_2SO_4$. After removal of solvent, the residue is distilled to afford 2-(2-bromoethyl)-thiopene 4 (6.1 g, 43%).

EXAMPLE 5

Preparation of Compound 5

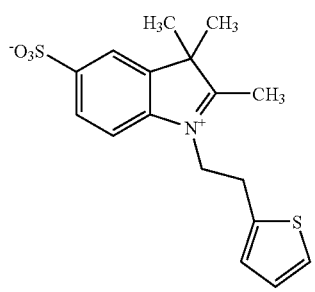

Compound 5

Compound 5 is prepared through the reaction of the potassium salt of 2,3,3-trimetylindolenium-5-sulfonate and 2-(2-bromoehtyl)-thiophene by the same procedure for preparation of Compound 3.

EXAMPLE 6

Preparation of Compound 6

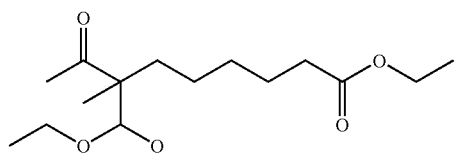

Compound 6

To the solution of sodium ethoxide (173.4 mmol, made from 4.0 g sodium in 200 mL dry ethanol) is added ethyl 2-methylacetoacetate (25 g, 173.4 mmol), followed by ethyl 6-bromohexanonate (44.5 g, 190.7 mmol). The mixture is heated to reflux for 12 hours. After cooling to room temperature, the mixture is filtered and the filtrate is concentrated. The residue is treated with 1M HCl to pH 1 and the aqueous solution is extacted with chloroform twice. The organic layer is washed with brine and dried over Na₂SO₄. After removal of solvent, the residue is purified on silica gel to afford 15 g of Compound 6.

EXAMPLE 7

Preparation of Compound 7

Compound 7

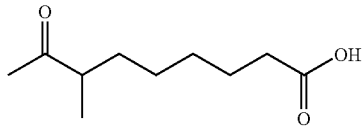

Compound 6 (7.2 g) in methanol (70 mL) is mixed with a solution of NaOH (3.3 g) in water (30 mL). The mixture is stirred at 55° C. for 3 hours. After removal of methanol, the residue is acidified with 1M HCl to pH 2. The aqueous solution is extracted with EtOAc twice. The organic layer is washed with brine and dried over Na₂SO₄. The crude product is purified with silica gel chromatography to yield Compound 7 (4.2 g).

EXAMPLE 8

Preparation of Compound 8

Compound 8

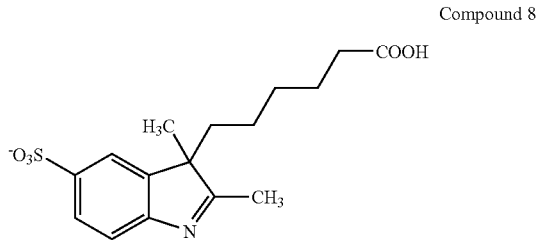

The mixture of 7-methyl-8-oxo-nonanoic acid 7 (4.2 g) and 4-hydrazinobenzenesulfonic acid (4.23 g) in acetic acid (30 mL) is heated to reflux for 8 hours. After removal of acetic acid, the residue is purified on silica gel to give Compound 8 (3.1 g).

EXAMPLE 9

Preparation of Compound 9

A solution of Compound 8 (3.1 g) and potassium acetate (1.1 g) in methanol (20 mL) is stirred at room temperature for 15 min. After removal of methnol, the resulting potassium salt is heated with 1,3-propanesultone (2.0 g) in 1,2-dichlorobenzene (5 mL) at 110° C. for 1.5 hour. The mixture is cooled to room temperature and the 1,2-dichlorobenzene is decanted. The solid is triturated with 2-propanol and the free powder is filtered and washed with 2-propanol and ether and dried under vacuum to yield Compound 9.

Compound 9

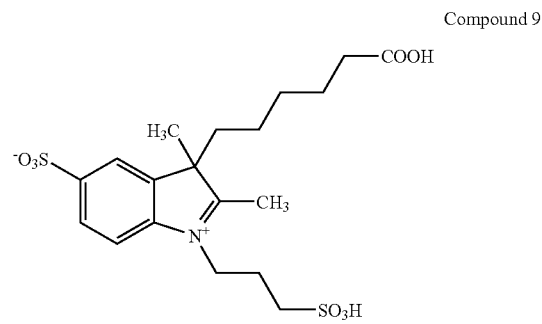

EXAMPLE 10

Preparation of Compound 10

A solution of compound 3 (100 mg, 0.265 mmol) and malonaldehyde bis(phenylimine)monohydrochloride (69 mg, 0.265 mmol) in acetic acid (0.5 mL) and acetic anhydride (0 5 mL) is heated at 120° C. for 1 hour. The completion of the reaction is monitored by absorption spectra in methanol. The solution of anyl intermediate is mixed with compound 9 (130 mg, 0.275 mol), then more acetic anhydride (0.5 mL) and pyridine (1.0 mL) is added. The mixture is heated for 30 min until the anyl intermediate disappeared (monitored by absorption spectra). The solution is cooled and the dye is precipatated with ethyl acetate. The crude product is collected by centrifugation and washed with ethyl acetate twice. The pure dye is obtained by preparative HPLC purification on C18 column as bright blue powder (40 mg).

Compound 10

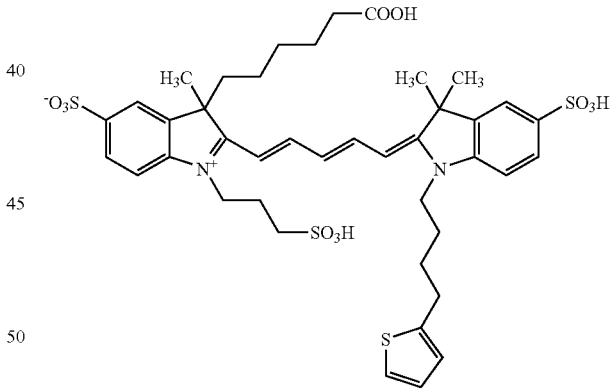

EXAMPLE 11

Preparation of Compound 11

To the mixture of 5-bromo-2,3,3-Trimethyl-3H-indole (12.0 g, 50 4 mmol), 2-thiopheneboronic acid (8.67 g, 67.8 mmol), Pd(PPh₃)₄ (1.45 g, 1.26 mmol) in toluene (200 mL) (flushed with nitrogen for 15 min) is added a solution of Na₂CO₃ (10.6 g) and tetrabutylammonium bromide (10.7 g) in water (55 mL). The mixture is heated to reflux for 8 hours. After cooling to room temperature, the mixture is diluted with water (200 mL). The organic layer is separated and washed with brine (2×100 mL) and dried over Na₂SO₄. After removal of solvent, the residue is purified on silica gel (3:1 hexane:ethyl acetate) to afford Compound 11 (10.8 g, yield: 89%).

Compound 11

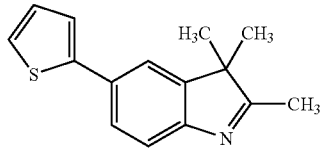

EXAMPLE 12

Preparation of Compound 12

Compound 12

A mixture of Compound 11 (4.3 g, 17.8 mmol) and 6-bromohexanoic acid (5.2 g, 26.7 mmol) in 1,2-dichlorobenzene (10 mL) is stirred at 120° C. overnight. After cooling to room temperature, the mixture is treated with ether. The crude sticky oil product is washed with ether twice and recrystallized in chloroform to afford 4.75 g of Compound 12.

EXAMPLE 13

Preparation of Compound 13

Compound 13

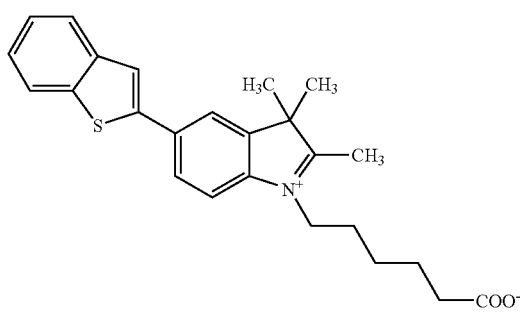

Compound 13 is analogously synthesized by the same procedure described above for the synthesis of compound 12.

EXAMPLE 14

Preparation of Compound 14

Compound 14

Compound 14 is synthesized by the same procedure described above for synthesis of Compound 12.

EXAMPLE 15

Preparation of Compound 15

Compound 15

Compound 15 is prepared by Fisher indole synthesis with 4-nitrophenylhydrazine and 3-methyl-2-butanone, followed by quartemizing with ethyl iodide.

EXAMPLE 16

Preparation of Compound 16

Compound 16

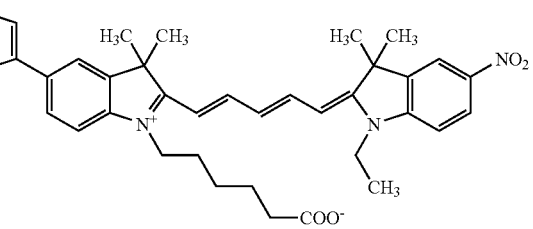

A solution of compound 12 (100 mg, 0.281 mmol) and malonaldehyde bis(phenylimine)monohydrochloride (76 mg, 0.295 mmol) in acetic acid (0.5 mL) and acetic anhydride (0.5 mL) is stirred at 120° C. for 1 hour. The completion of the reaction is monitored by absorption spectra in methanol. The solution of anyl intermediate is mixed with Compound 15 (101 mg, 0.281 mol), then more acetic anhydride (0.5 mL) and pyridine (1.0 mL) is added. The mixture is stirred for 30 min unitl the anyl intermediate disappears (monitored by absorption spectra). The solution is cooled and the dye is precipitated with ethyl ether. The solid is collected by centrifugation and washed with ether twice. The pure dye is obtained by silica gel chromatography.

EXAMPLE 17

Preparation of Compound 17

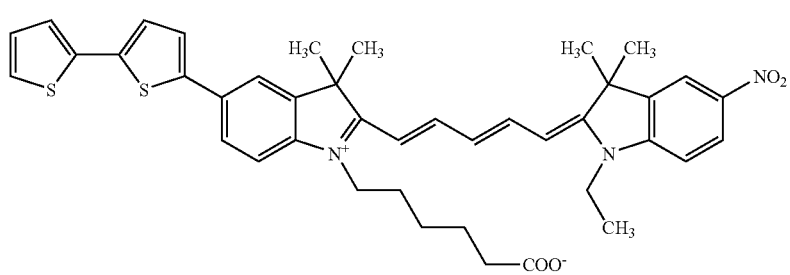

Compound 17

A solution of compound 14 (100 mg, 0.228 mmol) and bis(phenylimine)monohydrochloride (62 mg, 0.239 mmol) in acetic acid (0.5 mL) and acetic anhydride (0.5 mL) is stirred at 120° C. for 1 hour. The completion of the reaction is monitored by absorption spectra in methanol. The solution of anyl intermediate is mixed with Compound 15 (82 mg, 0.228 mol), then more acetic anhydride (0.5 mL) and pyridine (1.0 mL) is added. The mixture is stirred for 30 min until the anyl intermediate disappears (monitored by absorption spectra). The solution is cooled and the dye is precipitated with ethyl ether. The solid is collected by centrifugation and washed with ether twice. The pure dye is obtained by silica gel chromatography.

EXAMPLE 18

Preparation of Compound 18

A solution of compound 13 (100 mg, 0.246 mmol) and malonaldehyde bis(phenylimine)monohydrochloride (67 mg, 0.258 mmol) in acetic acid (0.5 mL) and acetic anhydride (0.5 mL) is stirred at 120° C. for 1 hour. The completion of the reaction is monitored by absorption spectra in methanol. The solution of anyl intermediate is mixed with indolenine 15 (89 mg, 0.246 mol), then more acetic anhydride (0.5 mL) and pyridine (1.0 mL) is added. The mixture is stirred for 30 min until the anyl intermediate disappeared (monitored by absorption spectra). The solution is cooled and the dye is precipitated with ethyl ether. The solid is collected by centrifugation and washed with ether twice. The pure dye is obtained by silica gel chromatography.

Compound 18

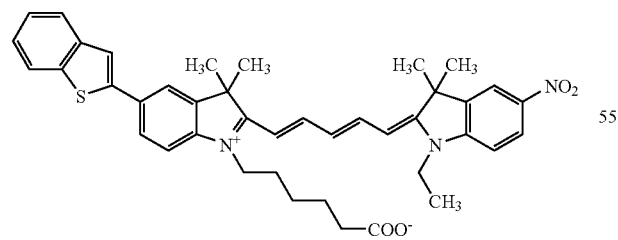

EXAMPLE 19

Preparation of Compound 19

A solution of compound 12 (100 mg, 0.281 mmol) and malonaldehyde bis(phenylimine)monohydrochloride (76 mg, 0.295 mmol) in acetic acid (0.5 mL) and acetic anhydride (0.5 mL) is stirred at 120° C. for 1 hour. The completion of the reaction is monitored by absorption spectra in methanol. The solution of anyl intermediate is mixed with 1,3-diethyl-2-methylimidazolium iodide (0.281 mol), then more acetic anhydride (0.5 mL) and pyridine (1.0 mL) is added. The mixture is stirred for 30 min until the anyl intermediate disappeared (monitored by absorption spectra). The solution is cooled and the dye is precipatated with ethyl ether. The solid is collected by centrifugation and washed with ether twice. The pure dye is obtained by silica gel chromatography.

Compound 19

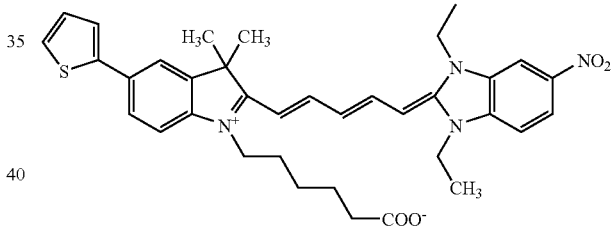

EXAMPLE 20

Preparation of Compound 20

Compound 20

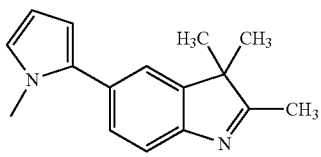

To the mixture of 5-bromo-2,3,3-trimethyl-3H-indole (50 mmol), 1-methyl-2-pyrroleboronic acid (68 mmol), Pd(PPh$_3$)$_4$ (1.3 mmol) in toluene (200 mL) (flushed with nitrogen for 15 min) is added a solution of Na$_2$CO$_3$ (11 g) and tetrabutylammonium bromide (10.7 g) in water (55 mL). The mixture is heated to reflux for 8 hours. After cooling to room temperature, the mixture is diluted with water (200 mL). The organic layer is separated and washed with brine (2×100 mL) and dried over Na$_2$SO$_4$. After removal of solvent, the residue is purified on silica gel (3:1 hexane:ethyl acetate) to afford Compound 20 (10.8 g, yield: 89%).

EXAMPLE 21

Preparation of Compound 21

The mixture of 2,3,3-trimethyl-5-(2-(1-methyl)pyrrolyl))-3H-indole (18 mmol) and 6-bromohexanoic acid (27 mmol) in 1,2-dichlorobenzene (10 mL) is stirred at 120° C. overnight. After cooling to room temperature, the mixture is treated with ether. The crude sticky oil product is washed with ether twice and recrystallized in chloroform to afford powder product compound 21 (yield: 4.8 g).

Compound 21

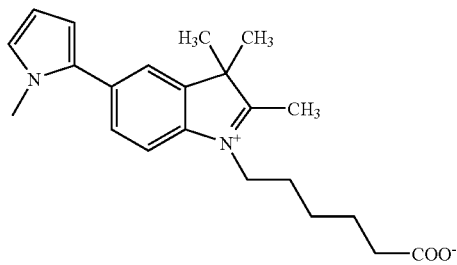

EXAMPLE 22

Preparation of Compound 22

Compound 22

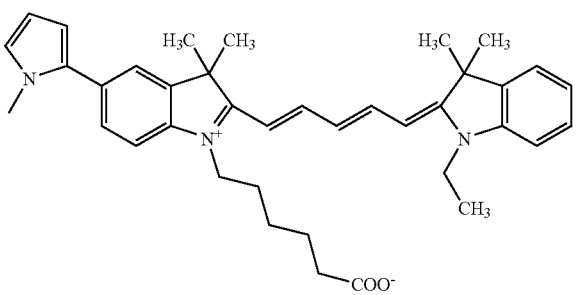

Compound 22 is analogously synthesized from Compound 21.

EXAMPLE 23

Preparation of Compound 23

Compound 23

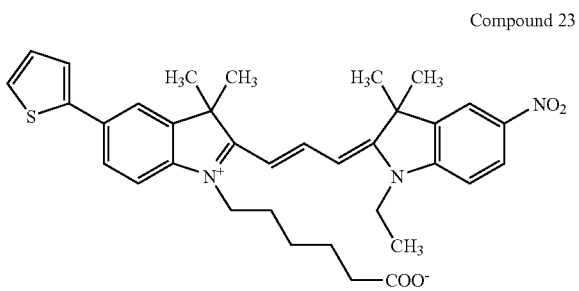

A solution of Compound 15 (100 mg, 0.278 mmol) and N,N'-diphenylformamidine (60 mg, 0.305 mmol) in acetic acid (0.5 mL) and acetic anhydride (0.5 mL) is stirred at room temperature for 1 hour. The completion of the reaction is monitored by absorption spectra in methanol. The solution of anyl intermediate is mixed with Compound 12 (99 mg, 0.278 mol), then more acetic anhydride (0.5 mL) and pyridine (1.0 mL) is added. The mixture is stirred at 110° C. for 30 min until the intermediate disappears (monitored by absorption spectra). The solution is cooled and the dye is precipitated with ethyl ether. The solid is collected by centrifugation and washed with ether twice. The pure dye is obtained by silica gel chromatography, 54 mg.

EXAMPLE 24

Preparation of Compound 24

Compound 24

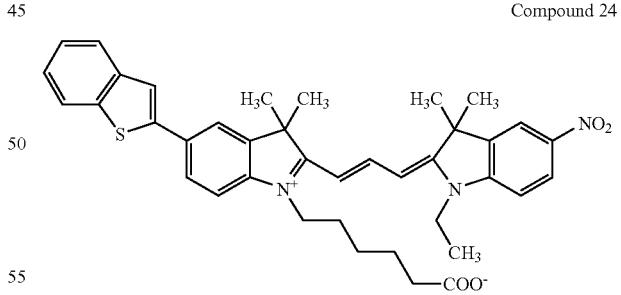

A solution of Compound 15 (100 mg, 0.278 mmon) and N,N'-diphenylformamidine (60 mg, 0.305 mmol) in acetic acid (0.5 mL) and acetic anhydride (0.5 mL) is stirred at room temperature for 1 hour. The completion of the reaction is monitored by absorption spectra in methanol. The solution of anyl intermediate is mixed with Compound 13 (113 mg, 0.278 mol), then more acetic anhydride (0.5 mL) and pyridine (1.0 mL) is added. The mixture is stirred at 110° C. for 30 min until the intermediate disappears (monitored by absorption spectra). The solution is cooled and the dye is precipitated with ethyl ether. The solid is collected by centrifugation and washed with ether twice. The pure dye is obtained by silica gel chromatography (42 mg).

EXAMPLE 25

Preparation of Compound 25

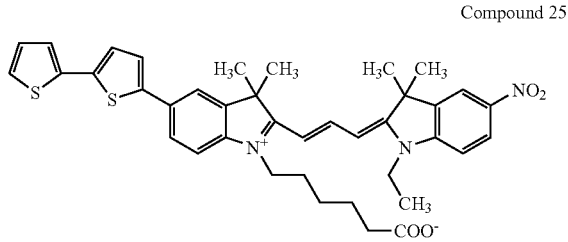

Compound 25

A solution of Compound 15 (100 mg, 0.278 mmon) and N,N'-diphenylformamidine (60 mg, 0.305 mmol) in acetic acid (0.5 mL) and acetic anhydride (0.5 mL) is stirred at room temperature for 1 hour. The completion of the reaction is monitored by absorption spectra in methanol. The solution of intermediate is mixed with Compound 14 (98 mg, 0.278 mol), then more acetic anhydride (0.5 mL) and pyridine (1.0 mL) is added. The mixture is stirred at 110° C. for 30 min until the intermediate disappears (monitored by absorption spectra). The solution is cooled and the dye is precipitated with ethyl ether. The solid is collected by centrifugation and washed with ether twice. The pure dye is obtained by silica gel chromatography (53 mg).

EXAMPLE 26

Preparation of Compound 26

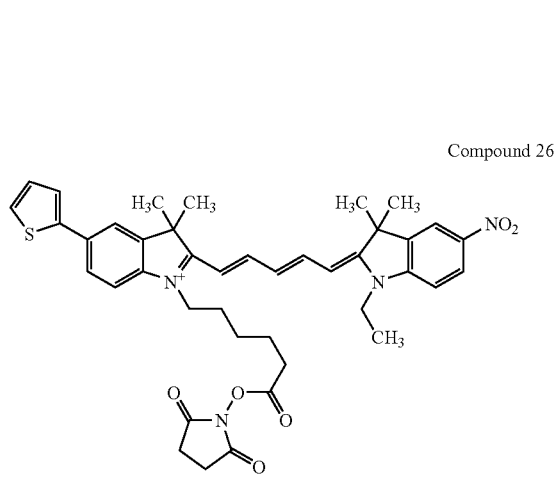

Compound 26

To 50 mg of Compound 16 in 1 mL of DMF is added 0.034 mL of triethylamine and 21 mg of 2-succinimido-1,1,3,3-tetramethyluronium tetrafluoroborate. The mixture is stirred at room temperature for 30 minutes and evaporated to yield Compound 26.

EXAMPLE 27

Preparation of Compound 27

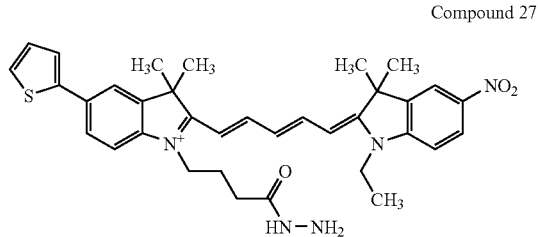

Compound 27

To Compound 26 in acetonitrile is added 3 equivalents of triethylamine and 1.2 equivalents anhydrous hydrazine. The mixture is stirred at ambient temperature for 15 minutes. The product is precipitated with 4 volumes of ethyl acetate and purified by HPLC.

EXAMPLE 28

Preparation of Compound 28

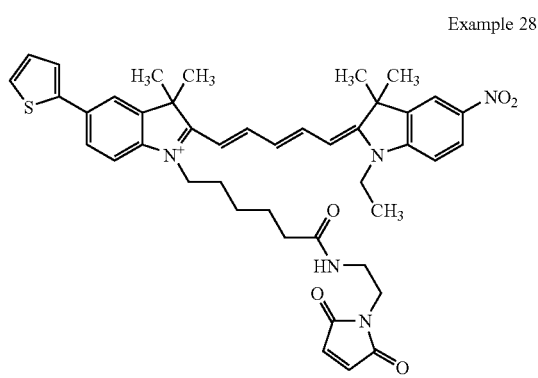

Example 28

To Compound 26 in acetonitrile at room temperature is added 4 equivalents of triethylamine and 1.2 equivalents of N-(2-aminoethyl)maleimide, trifluoroacetic acid salt. The

EXAMPLE 29

Preparation of Compound 29

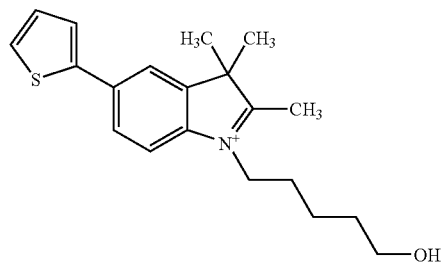
Compound 29

Compound 29 is preparaed by the quaternization of compound 11 with 6-bromohexanol analogous to the procedure of compound 12.

EXAMPLE 30

Preparation of Compound 30

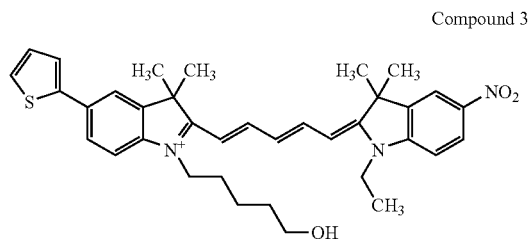
Compound 30

Compound 30 is preparaed from compound 29 analogous to the procedure of compound 16.

EXAMPLE 31

Preparation of Compound 31

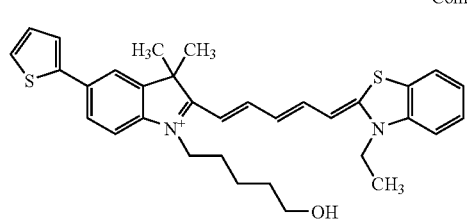
Compound 31

Compound 31 is prepared in the same manner as Compound 30 except starting with 2-methyl-1-ethylbenzothiazolium iodide, which is prepared by reaction of ethyl iodide and 2-methylbenzothiazole at room temperature.

EXAMPLE 32

Preparation of Compound 32

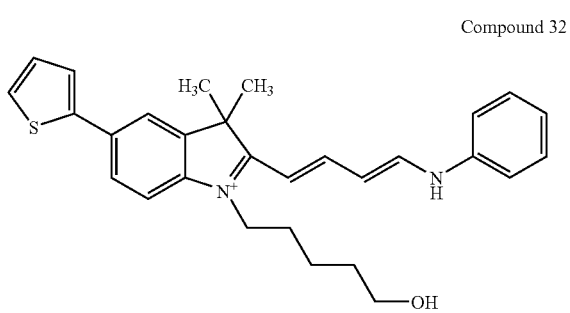
Compound 32

A mixture of 2 g of Compound 29 and 3 g of N-(5-anilino-2,4-pentadienylidene)aniline hydrochloride in 30 mL of acetic anhydride is heated at 120° C. for 30 minutes. The reaction is monitored by absorption spectrum, and the crude intermediate is used as is.

EXAMPLE 33

Preparation of Compound 33

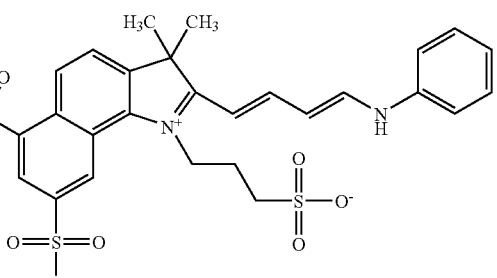
Compound 33

Compound 33 is prepared by quaternization of 1,1,2trimethylbenzindoleninium 1,3-disulfonate [Bioconjugate Chem., 356-362 (1996)] with propanesultone and then heated with 2 equivalents of malonaldehyde dianil hydrochloride in acetic acid with catalytic amount of triethylamine to yield Compound 32.

EXAMPLE 34

Preparation of Compound 34

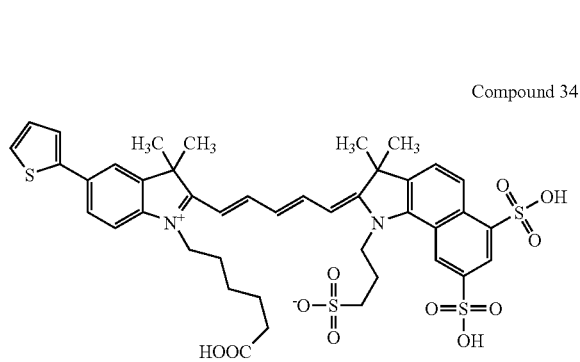

Compound 34

Compound 34 is prepared by stirring one equivalent each of Compounds 12 and 33 in the presence of 3 equivalents of tri ethyl amine and one equivalent of acetic anhydride in DMF at room temperature for one hour to yield Compound 34. Compound 34 is optionally converted to its corresponding succinimidyl ester as described in Example 26.

EXAMPLE 35

Preparation of Compound 35

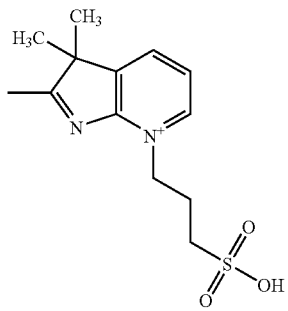

Compound 35

2-Amino-3-hydroxypyridine (14.48 g) is triacetylated by heating with 3 equivalents of acetic anhydride at 120-130° C. for 4 hours to yield, after silica gel column purification, 10.3 g of 3-acetoxy-2,2-diacetylimidopyridine. This compound is heated for 2 days at 65° C. with 3 equivalents of methyl tosylate to yield 7 g of 3 acetoxy 1 methyl-2-acetimido-1,2-dihydropyridine, p-toluenesulfonic acid salt. The 2-methy-loxazolo[4,5-b]pyridine is then generated in situ when this dihydropyridine is treated with triethylamine.

EXAMPLE 36

Preparation of Compound 36

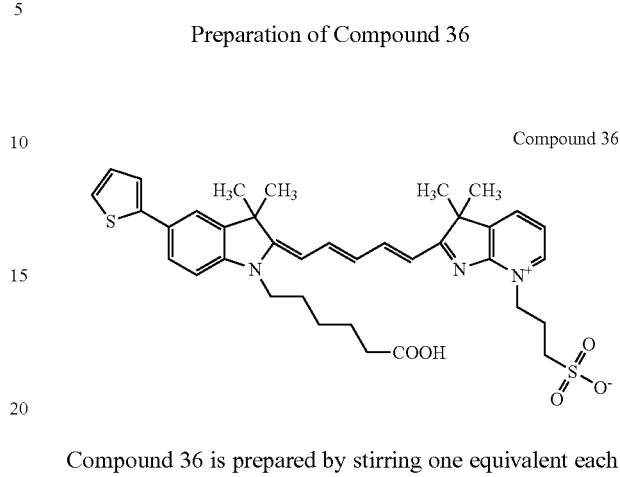

Compound 36

Compound 36 is prepared by stirring one equivalent each of Compounds 12 and 35 in the presence of 3 equivalents of triethylamine and one equivalent of acetic anhydride in DMF at room temperature for one hour to yield Compound 36. Compound 36 is optionally converted to its corresponding succinimidyl ester as described in Example 26.

EXAMPLE 37

Preparation of Compound 37

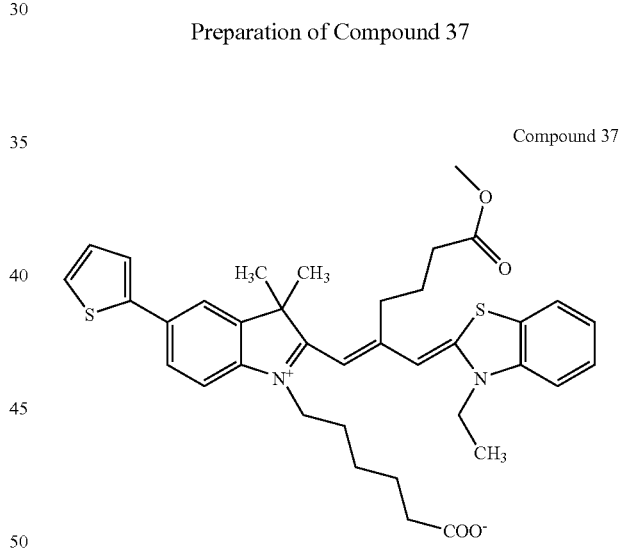

Compound 37

To 1.7 g of 2,3-dimethyl-6-sulfobenzothiazolium tosylate in 20 mL of pyridine at room temperature is added 1 mL of methyl 5-chloro-5-oxovalerate. The mixture is heated at 50-60° C. for 3 hours. The pyridine solvent is removed under reduced pressure, and the reaction is worked up with chloroform and brine, and purified by silica gel column to yield 0.5 g of 2-(5-methoxycarbonyl-2-oxopentylidene)-3-methyl-3H-benzothiazole. A mixture of 0.45 g of this benzothiazole and 0.45 g of phosphorous oxychloride in 5 mL of dichloroethane is heated at reflux for 2 hours to generate 2-(2-chloro-2-methoxycarbonylpropylvinyl)-3-methylbenzothiazolium chloride. The volatile components are evaporated and the crude chloride is used without further purification. The crude chloride and 0.5 g of Compound 12 is stirred in 5 mL of dichloroethane in the presence of 0.45 mL of triethylamine for 2 hours. The volatile components are removed under reduced pressure, and the residue is dissolved in 5 mL of methanol and added dropwise to a solution of 4.5 g of sodium iodide in 30 mL water. The sticky solid is purified by HPLC to yield Compound 37.

EXAMPLE 38

Preparation of Compound 38

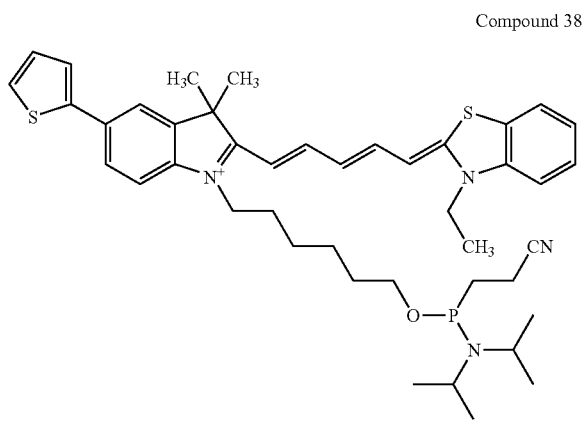

Compound 38

To 150 mg of Compound 31 in 2 mL of methylene chloride at 0° C. under nitrogen is added sequentially 0.19 mL of diisopropylethylamine and 0.23 mL of 2-cyanoethyl diisopropylchlorophosphoramidite. The reaction mixture is stirred for 5 minutes then poured onto sodium bicarbonate and extracted with methylene chloride. The methylene chloride is removed under reduced pressure to yield the phosphoramidite derivative (Compound 38). The phosphoramidite derivative is useful for the preparation of quenching compound-labeled oligonucleotides using an automated synthesizer.

EXAMPLE 39

Preparation of Compound 39

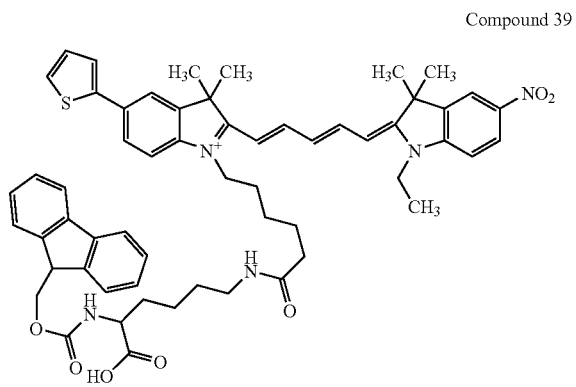

Compound 39

To 0.5 g of Compound 26 in 10 mL of DMF and 3 mL of pyridine at room temperature is added 0.57 g of alpha-FMOC-L-lysine hydrochloride. The mixture is stirred at room temperature for 6 hours. The solution is poured into 130 mL of cold 1 M HCl. The crude residue is filtered and dried in vacuo then purified on a silica gel column to yield of the FMOC-L-lysine 39.

EXAMPLE 40

Evaluation of Quenching Compound Fluorescence

Quantum yield measurements are made by comparing the integrated fluorescence emission of the quenching compound of the invention with the integrated fluorescence of nile blue A (QY=0.23 in ethanol) at equal dye absorbance, at the excitation wavelength. The fluorescence of buffer alone is subtracted from that of the sample for each measurement. The quenching compounds of the invention are weakly fluorescent or essentially non-fluorescent.

EXAMPLE 41

Quenching of a Fluorescent Dye-Labeled Protein

Albumin from bovine serum (BSA), previously labeled with 6.3 moles of fluorescein per mole of protein, is dissolved in 0.1 M bicarbonate buffer (pH 8.3) to give a solution concentration of 5 mg/mL. Three aliquots of 0.4 mL (2 mg) are removed from the resulting solution, and are treated with DMSO solutions of Compound 26 equivalent to 5, 10, and 20 molar equivalents of Compound 26 per mole of BSA, respectively. Each of the resulting solutions are incubated for one hour at room temperature. Hydroxylamine is added (to a final concentration of 0.15 M) to stop the conjugation reaction. After the samples are incubated for 30 minutes at room temperature, they are subjected to size exclusion chromatography in 0.1 M sodium phosphate buffer (pH 8.0).

EXAMPLE 42

Preparation of Oligonucleotide Conjugates of Quenching Compounds

Eighteen-base oligonucleotide conjugates of quencher dyes are prepared using standard methods. Typically, a 6-(N-trifluoroacetylamino)hexyl is synthetically incorporated on the 5' end of the oligonucleotide of interest as a phosphoramidite, and the TFA protection group is then removed under basic conditions. The resulting conjugate is subsequently reacted with a succinimidyl ester derivative of a quenching compound of the invention. Specifically, the succinimidyl ester derivative is dissolved in DMSO at a concentration of about 12.5 mg/mL. The amine-modified oligonucleotide is dissolved in water at a concentration of 25 mg/mL. A fresh solution of 0.1 M sodium borate, pH 8.5 is prepared. In a microfuge tube, 4 uL of the oligonucleotide solution is combined with 200 ug of the quenching compound solution and 100 uL sodium borate buffer. Samples are incubated 4 hours to overnight at room temperature, and the nucleic acids are precipitated by addition of 0.1 volume 0.3 M NaCl and 2.5 volumes cold absolute ethanol. Samples are incubated for 30 minutes at −20° C. and centrifuged in a microfuge for 30 minutes. The supernatant fluid is decanted and the pellet dried under vacuum.

Alternatively, the oligonucleotide conjugate is prepared by reaction of a maleimide derivative of a quenching compound of the invention with an oligonucleotide that has been derivatized by a thiol that has been incorporated via a phosphoramidite.

Conjugates are purified by reverse phase HPLC, using a C18 reverse phase column and a gradient of 5-95% acetonitrile in 0.1 M TEAA, pH 7. Absorbance and fluorescence emission spectra are determined in 10 mM Tris-HCl, 1 mM EDTA, pH 7.5. Quantum yield measurements are made as described above (Example 40). Oligonucleotide conjugates of the quenchers are weakly fluorescent or essentially non-fluorescent.

EXAMPLE 43

Preparation of an Oligonucleotide Conjugate Substituted with Both a Fluorophore and a Quenching Compound Oligonucleotides conjugated to a Cy5 fluorophore at one terminus and a quenching compound of the invention at the other terminus are prepared using a 3' or 5' Cy3 (or Cy5) phosphoramidite and an amine modifier at the other terminus of the oligonucleotide, followed by labeling with a succinimidyl ester derivative of the invention (as described above in Example 43), or by synthesis of oligonucleotides containing an amino modifier on one terminus and a thiol at the other terminus, followed by sequential reaction with a maleimide derivative and succinimidyl ester derivative of the fluorophore and quenching compound, or vice versa. The fluorescence of the resulting conjugates is measured at equal conjugate concentration. Selected compounds of the instant invention quench the fluorescence of fluorescein much more efficiently than does DABCYL.

EXAMPLE 44

Preparation of Doubly Labeled Oligonucleotide Conjugates

Random-sequence oligonucleotides 10, 20, 30 and 40 bases in length are labeled with Cy5 at their 3' terminus using a Cy5 phosphoramidite, and with Compound 26 at their 5' terminus, by reacting the amine-modified oligonucleotide with the succinimidyl ester derivative. Resulting conjugates are purified by reverse phase HPLC. The fluorescence of equal amounts of these doubly labeled conjugates is determined relative to the fluorescence of Cy5 conjugates lacking the quencher dye.

EXAMPLE 45

Hybridization of Doubly-Labeled Oligonucleotide Conjugates to Unlabeled Complementary Olizonucleotides Solutions are prepared containing 1 ug/mL 18-base oligonucleotide conjugates of a quenching compound of the invention attached to the 5' terminus, as well as a Cy5 fluorophore on the 3' terminus. The oligonucleotide conjugates are hybridized with 40 ug/mL reverse complement oligonucleotide in TE buffer at pH 9.0. The samples are heated for 10 minutes at 65° C., allowed to cool slowly to room temperature, and are then incubated at room temperature for 60 minutes, protected from light. A portion of each sample is transferred to a microplate well and the fluorescence emission of the sample is determined at ~670 nm (with 650 nm excitation). The fluorescence is compared to the fluorescence of a buffer solution alone. The conjugates of the invention exhibit an increase in fluorescence upon hybridization. Because the quenched oligonucleotides initially exhibited extremely low fluorescence, they show larger increases upon hybridization, and therefore the conjugates that are the most efficiently quenched prior to hybridization exhibit the largest increase in fluorescence. This property is utilized to formulate a homogenous assay method to detect the presence of to specific complementary DNA sequences in a sample. Several of the compounds of the invention quench fluorescence more efficiently than DABCYL in this application. Similarly, doubly labeled oligonucleotides that form structures that enhance quenching, such as hairpin or stem loop structures, as in BEACON probes, can also be used in this application.

EXAMPLE 46

Hybridizing Oligonucleotide Conjugates of Quenching Compounds with Fluoroohore Labeled Oligonucleotides Oligonucleotides conjugated to a quenching compound at one terminus quench the fluorescence of fluorophore labeled nucleotides upon hybridization. Labeled oligonucleotides are prepared as described above (Examples 43 and 44), and hybridized with their reverse complements. Samples containing 2 ug/mL quenching compound-labeled 18 base oligonucleotides and 200 ng/mL Cy5-labeled reverse complement oligonucleotides in 10 mM Tris-HCl, 1 mM EDTA, pH 9.0, are hybridized and their fluorescence is determined as described above (Example 40). The quenching compound oligonucleotides efficiently quench the fluorescence of Cy5 that is localized at the same end of hybridized oligonucleotides, but quench the fluorescence of distant fluorophores more poorly.

EXAMPLE 47

Quenching Fluorescence of Nucleotides Added Enzymatically to the 3' End of a Primer An eighteen-base oligonucleotide is labeled with Compound 26 on its 5' terminus, as described in Example 42. The resulting conjugate is incubated with terminal deoxynucleotidyl transferase under standard assay conditions for 3' end elongation, in the presence of fluorophore-labeled dUTP conjugates, as follows: The oligonucleotide conjugate (650 ng) is incubated with 1 uL of 25 mM fluorophore-labeled nucleotide, 0.5 mM $CoCl_2$, and 0.2 M potassium cacodylate, 25 mM Tris-HCl, pH 6.6, 2 mM DTT, and 250 ug/mL bovine serum albumin for 60 minutes at 37° C. A one-fifth volume of a solution containing 50% glycerol and 0.01% bromophenol blue is added to each reaction, and the samples are separated by electrophoresis on a 20% polyacrylamide/8 M urea mini-gel in TBE buffer (45 mM Tris-borate, 1 mM EDTA), under conditions that resolve single nucleotide additions to the oligonucleotide. Samples containing oligonucleotides that are lacking the quenching compound are processed in parallel, for use as size standards. Gels are visualized using a 300-nm UV transilluminator combined with Polaroid black and white photography, or using a laser scanner. The gels are post-stained with a fluorescent nucleic acid stain, such as ethidium bromide, and band fluorescence is visualized in the same way. The size of the oligonucleotides is determined based on comparisons of electrophoretic migration with the unlabeled standard. Quenching is detected as lack of fluorescence or visibility of a band of a particular size from the pattern visible in the standard. Where the fluorophore is Cy5 dye, the label fluorescence is readily quenched by the 5'-bound quenching compound.

This technique is useful as a gel-based method for quantitating terminal transferase activity. Enzyme activity in an unknown sample is determined by comparison of the number of added nucleotides per template or the number of templates with added nucleotides of a certain length with the numbers obtained using a standard amount of enzyme activity following a standard reaction time interval.

EXAMPLE 48

Quenching of a Fluorescent Oligonucleotide by Enzymatic Incorporation of a Quenching Compound Conjugate of Nucleotide Triphosphate Via Primer Extension A short oligonucleotide, having 6 to about 20 bases, is labeled with a fluorophore such as Cy5 dye, on its 5' terminus, and then purified via HPLC. For template-driven reactions, the oligonucleotide is hybridized to an appropriate template, and incubated with a quenching compound-labeled nucleotide or deoxynucleotide in an appropriate buffered solution, in the presence of samples thought to contain an appropriate DNA or RNA polymerase. Enzyme activity is determined by measuring the rate of fluorescence loss from the solution, versus the rate of loss observed from solutions containing known amounts of enzyme activity. Terminal deoxynucleotidyltransferase activity is assayed by determining the rate of fluorescence loss from the solution upon incubation with samples thought to contain terminal deoxynucleotidyltransferase activity. For measurement of terminal deoxynucleotidyl transferase activity, fluorophore-labeled templates are incubated with quenching compound-labeled nucleotides for a set time interval, and fluorescence is measured in a fluorescence microplate reader or fluorometer.

To measure reverse transcriptase activity, 2 ug mRNA is combined with 5 ug fluorophore labeled poly dT (16) oligomer in 10 mM Tris-HCl, pH. 8.0, 1 mM EDTA; the mixture is heated to 70° C. for 10 minutes and then chilled on ice. A solution containing 2 uL reverse transcriptase (200 units/uL for the standard, or unknown amounts), 500 uM dATP, 500 uM dCTP, 500 uM dGTP, 200 uM dTTP, and 60 uM quenching compound-labeled dUTP is prepared and added to the RNA. The reaction is allowed to proceed for 2 hours at 42° C. The fluorescence of the solution is measured in a fluorescence microplate reader or fluorometer versus a standard. The decrease in fluorescence in comparison to samples lacking enzyme activity is directly related to the activity of the enzyme in the reaction.

To measure Klenow DNA polymerase activity, 1 ug random sequence 9-mer oligonucleotides labeled with a fluorescent dye are combined with 2.5 ug genomic DNA in 10 mM Tris-HCl, pH 8.0, 1 mM EDTA. The mixture is boiled for 2 minutes and chilled on ice. A reaction mixture containing 25 uM dATP, 25 uM dCTP, 25 uM dGTP and 10 uM dTTP, plus 40 uM quenching compound-labeled dUTP in 1 mM Tris-HCl, pH 7.5, 5 mM NaCl, 0.01 mM EDTA, pH 8.0, 5 mM dithiothreitol is combined with samples thought to contain DNA polymerase. The reaction mixture is combined with the DNA mixture and incubated at 37° C. for 2 hours. The fluorescence of the sample is measured versus standards, as described in Example 40.

EXAMPLE 49

Using Quenching Compounds to Measure Nuclease Activity

Oligonucleotide conjugates labeled with both a quenching compound at one terminus and a fluorophore at the other terminus are prepared as described in Examples 43 and 44. For measuring single-stranded nuclease activity, the conjugates are incubated in the presence of samples thought to contain nuclease activity in the presence of an appropriate buffer and the resulting fluorescence increase in the sample is compared to that obtained using standards of known nuclease concentration. To measure double-stranded nuclease activity, double-stranded templates are prepared by hybridizing two oligonucleotides to one another, or by chemically modifying a double-stranded template using reagents such as platinum complexes of fluorophores and quenchers (as described in U.S. Pat. Nos. 5,714,327 and 6,133,038), or by using an enzyme such as a terminal transferase to add nucleotides to the end of a template as described in Examples 47 and 48. Samples thought to contain nuclease activity are incubated with such templates in the presence of appropriate buffers and the increase in fluorescence compared to a standard, as described in Example 40.

EXAMPLE 50

Using Quenching Compounds to Measure Ligase Activity

Oligonucleotide hexamers labeled at the 5' terminus with a quenching compound are prepared as described in Example 42 and 43. Oligonucleotide hexamers labeled with a fluorophore at the 3' terminus and phosphate at the 5' terminus are analogously prepared except that the phosphate is alternatively applied by standard methods using a phosphoramidite or by enzymatic means, such as T4 polynucleotide kinase.

A reaction mixture is prepared that contains about 5 ug of each oligonucleotide conjugate, 0.5 mM ATP, and samples thought to contain ligase activity, in 1 mM MgCl$_2$, 2 mM dithiothreitol, 5 ug/mL bovine serum albumin, and 5 mM Tris-HCl, pH 7.7, in a volume of 20 uL. The reaction mixtures are incubated for 2 hours to overnight at 22° C., and the sample fluorescence is measured. As the quenching compound-labeled oligonucleotides do not contain a free 5' phosphate, they cannot ligate to one another, and as the fluorophore-labeled oligonucleotides do not contain a free 3' hydroxyl, they cannot ligate to one another. Thus the only products of ligation will be a dimer of the two oligonucleotides and the fluorescence decrease observed during the course of the reaction is a measure of ligase activity. Alternatively, RNA oligonucleotides are used as templates to measure RNA ligase activity or splicing activity.

EXAMPLE 52

Preparation of Quenched Double-Stranded DNA

Oligonucleotides are prepared that are either labeled with a fluorophore at a strand terminus, or within the oligonucleotide sequence itself, using standard methods as described above. The oligonucleotides are then used as primers for PCR or are otherwise enzymatically extended using standard methods. A quenching compound platinum complex is prepared (as described in U.S. Pat. No. 5,714,327) and dissolved in water at a final concentration of 1 mg/mL. DNA (500 ng) is combined with 1.5 ug of the quenching compound platinum complex and incubated in a total volume of 25 uL water for 15 minutes at 65° C. The reaction is chilled in an ice bath to stop it. The quenched DNA is not visible after gel electrophoresis, even when stained with a fluorescent nucleic acid stain or incubation in solution with a fluorescent nucleic acid stain.

EXAMPLE 53

Using Quenching Compounds to Assay Topoisomerase Activity

Quenched DNA is prepared as described above, using a circular single stranded DNA template, such as an M13 or OX174 phage DNA genome, and a quenching compound platinum complex (prepared as described in U.S. Pat. No. 5,714,327). A fluorophore-labeled oligonucleotide is then hybridized to the quenched DNA. Samples thought to contain topoisomerase activity are combined with the template under optimal reaction conditions for the enzyme, and the reaction is allowed to proceed for an appropriate period of time. Enzyme activity is measured as fluorescence increase for the solution, using a fluorescence microplate reader or fluorometer.

EXAMPLE 54

Detection of MMP-2 Activity and MMP-2 Assay Kit

The matrix metalloproteinases (MMPs) constitute a family of zinc-dependent endopeptidases that function within the extracellular matrix. These enzymes are responsible for the breakdown of connective tissues and are important in bone remodeling, the menstrual cycle and repair of tissue damage. While the exact contribution of MMPs to certain pathological processes is difficult to assess, MMPs appear to have a key role in the development of arthritis as well as in the invasion and metastasis of cancer.

MMP-2 is an important target for inhibitor screening due to its involvement in diseases such as cancer and arthritis.

Compound 19-Lys-Pro-Leu-Ala-Nva-Asp(Cy5)-Ala-Arg-NH2 is synthesized by the standard FMOC solid phase synthesis as described in Fmoc Solid Phase Peptide Synthesis: A Practical Approach, by Weng C. Chan, Oxford University Press, 2003. 50 µM the FRET peptide is incubated with 4 nM MMP-2 or without MMP-2 (control) at room temperature. The fluorescence signal is recorded on a fluorescence microplate reader at Ex/Em=650±40 nm/670±40 nm. The recording is started as soon as the enzymatic reaction is initiated. The result is shown in FIG. 11.

The invention claimed is:
1. A compound having the following structure:

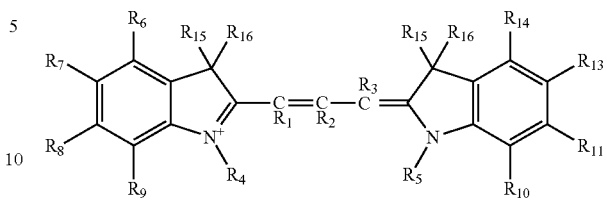

wherein $R_1$ to $R_3$, $R_6$, $R_8$ to $R_{11}$ and $R_{13}$ to $R_{16}$ are hydrogen, alkyl having from 1-20 carbons, alkoxy having from 1-20 carbons, trifluoromethyl, halogen, methylthio, sulfonyl, carbonyl, hydroxyl, amino, thiol, or nitro, and wherein $R_4$ is a chemically reactive group, and wherein $R_5$ is an alkyl having from 1-20 carbons, and wherein $R_7$ is a thiophene or a substituted thiophene.

2. The compound according to claim 1, wherein the chemically reactive group is a carboxylic acid, an activated carboxylic ester, a sulfonyl chloride, an isocyanate, an isothiocyanate, an acyl azide, an aldehyde, an anhydride, an acyl chloride, an aziridine, an epoxide, a halotriazine, an imido ester, a haloacetamide, a maleimide, an alcohol, a phosphoramidite, an aryl azide, a reactive platinum complex or psoralen.

3. The compound according to claim 2, wherein R15 and R16 are hydrogen or alkyl having from 1-20 carbons.

4. The compound according to claim 2, wherein $R_{13}$ is trifluoromethyl, halogen, methylthio, sulfonyl, carbonyl, hydroxyl, amino, thiol, or nitro.

5. The compound according to claim 2, wherein $R_1$ to $R_3$ are hydrogen.

6. The compound according to claim 2, wherein $R_8$ to $R_{11}$ are hydrogen.

7. The compound according to claim 3, wherein $R_{15}$ and $R_{16}$ are alkyl having from 1-20 carbons.

8. The compound according to claim 7, wherein the chemically reactive group is a carboxylic acid, an activated carboxylic ester, an acyl azide or a haloacetamide.

9. The compound according to claim 8, wherein $R_{13}$ is trifluoromethyl, halogen, methylthio, sulfonyl, carbonyl, hydroxyl, amino, thiol, or nitro.

10. The compound according to claim 9, wherein $R_1$ to $R_3$ are hydrogen.

* * * * *